US008709719B2

(12) United States Patent
Cohen et al.

(10) Patent No.: US 8,709,719 B2
(45) Date of Patent: Apr. 29, 2014

(54) ZNF217 A NEW PROGNOSTIC AND PREDICTIVE BIOMARKER OF RECURRENT INVASIVE AND METASTATIC PHENOTYPES IN BREAST CANCER

(75) Inventors: Pascale Cohen, Lyons (FR); Julie Vendrell, Villeurbanne (FR); Pierre Roux, Saint Gely du Fesc (FR)

(73) Assignees: Centre Leon Berard (FR); Universite Claude Bernard Lyon 1 (FR)

( * ) Notice: Subject to any disclaimer, the term of this patent is extended or adjusted under 35 U.S.C. 154(b) by 51 days.

(21) Appl. No.: 13/383,693

(22) PCT Filed: Jul. 19, 2010

(86) PCT No.: PCT/EP2010/060381
§ 371 (c)(1),
(2), (4) Date: Jan. 12, 2012

(87) PCT Pub. No.: WO2011/007013
PCT Pub. Date: Jan. 20, 2011

(65) Prior Publication Data
US 2012/0107826 A1 May 3, 2012

Related U.S. Application Data

(60) Provisional application No. 61/226,304, filed on Jul. 17, 2009.

(30) Foreign Application Priority Data

Jul. 17, 2009 (EP) ..................................... 09165733

(51) Int. Cl.
*C12Q 1/68* (2006.01)
(52) U.S. Cl.
USPC ......................................................... 435/6.1
(58) Field of Classification Search
CPC combination set(s) only.
See application file for complete search history.

(56) References Cited

U.S. PATENT DOCUMENTS

2004/0209290 A1* 10/2004 Cobleigh et al. ................... 435/6
2008/0311573 A1* 12/2008 Lillie et al. ......................... 435/6

FOREIGN PATENT DOCUMENTS

| EP | 0960197 A1 | 12/1999 |
| EP | 2113566 A1 | 11/2009 |
| WO | 98/02539 A1 | 1/1998 |
| WO | 02/06526 A1 | 1/2002 |
| WO | 03/079748 A2 | 10/2003 |
| WO | 2006/065940 A2 | 6/2006 |

OTHER PUBLICATIONS

Bhargava et al (Mod Pathol, 2005, 18(2): 1027-1033).*
Sun et al (Nan Fang Yi Ke Da Xue Bao, 2009, 29(4): Abstract).*
Collins et al (PNAS, 1998, 95: 8703-8708).*
Buck et al (Biotechniques, 1999, 27(3):528-536).*
PCT/EP2010/060381 International Search Report issued Jul. 10, 2010.
PCT/EP2010/060381 International Preliminary Report on Patentability issued Jan. 17, 2012.
Database Medline, Accession No. NLM16793610, Jun. 2006.
Huang, et al., "ZNF217 Suppresses Cell Death Associated with Chemotherapy and Telomere Dysfunction," Human Molecular Genetics, 2005, vol. 14, No. 21, 3219-3225.
Sun, et al., "Silencing of ZNF217 Gene Influences the Biological Behavior of a Human Ovarian Cancer Cell Line," International Journal of Oncology. 32: 1065-1071, 2008.
Quinlan et al., "Amplification of Zinc Finger Gene 217 (ZNF217) and Cancer: When Good Fingers Go Bad," Biochemica et Biophysica Acta, 1775 (2007) 333-340.
Bloom, etal., "Histological Grading and Prognosis in Breast Cancer," Br. J. Cancer, 11, (1957) 359-377.
Blows, et al., "Subtyping of Breast Cancer by Immunohistochemistry to Investigate a Relationship Between Subtype and Short and Long Term Survival: A Collaborative Analysis of Data for 10,159 Cases from 12 Studies," PLos Medicine, May 2010, vol. 7, Issue 5, e1000279.
Chanrion, et al., "A Gene Expression Signature that Can Predict the Recurrence of Tamoxifen-Treated Primary Breast Cancer," Clin Cancer Res., Mar. 2008, 14(6): 1744-1752.
Cheang, et al., "Ki67 Index, HER2 Status, and Prognosis of Patients with Luminal B Breast Cancer," JNCI, vol. 101, Issue 10, May 20, 2009.
Chen, et al., "A Small Interfering CD147-Targeting RNA Inhibited the Proliferation, Invasiveness, and Metastatic Activity of Malignant Melanoma," Cancer Res, 2006, 66: 11323-11330.
Collins, et al., "Comprehensive Genome Sequence Analysis of a Breast Cancer Amplicon," Genome Research, 11: 1034-1042, 2001.
Collins, et al., "Positional Cloning of ZNF217 and NABC1: Genes Amplified at 20q13.2 and Overexpressed in Breast Carcinoma," Proc. Natl. Acad. Sci. USA, vol. 95, 8703-8708, Jul. 1998.
Demirpence, et al., "MVLN Cells: A Bioluminescent MCF-7-Derived Cell Line to Study the Modulation of Estrogenic Activity," J. Steroid Biochem. Molec. Biol., vol. 46, No. 3, 355-364, 1993.
Galaup, et al., "Angiopoietin-like 4 Prevents Metastasis Through Inhibition of Vascular Permeability and Tumor Cell Motility and Invasiveness," PNAS, Dec. 5, 2006, vol. 103, No. 49, 18721-18726.
Ghayad, et al., "Endocrine Resistance Associated with Activated ErbB System in Breast Cancer Cells is Reversed by Inhibiting MAPK or PI3L Akt Signaling Pathways," Int. J. Cancer, 126, 545-562, 2009.
Ginestier, et al., "Prognosis and Gene Expression Profiliing of 20q13-Amplified Breast Cancers," Clin Cancer Res, 2006, 12(15), Aug. 1, 2006.
Girault, et al., "Expression analysis of DNA Methyltransferases 1, 3A, and 3B in Sporadic Breast Carcinomas," Clin Cancer Res, 2003, 9: 4415-4422.
Glondu, et al., "Down-regulation of Cathespsin-D Expression by Antisense Gene Transfer Inhibits Tumor Growth and Experimental Lung Metastasis of Human Breast Cancer Cells," Oncogene, (2002), 21, 5127-5134.
Gupta, et al., "Cancer Metastasis: Building a Framework," Cell, 127, Nov. 17, 2006.

(Continued)

*Primary Examiner* — Sean Aeder
(74) *Attorney, Agent, or Firm* — Banner & Witcoff, Ltd.

(57) ABSTRACT

The present invention relates to methods for determining the prognosis of a cancer. The methods involve determining the level of expression of the ZNF217 gene in a cancer cell sample or in a tumor sample wherein over-expression of ZNF217 is correlated with likelihood of metastasis and with likelihood of relapse/recurrence of the cancer.

23 Claims, 19 Drawing Sheets

(56) References Cited

OTHER PUBLICATIONS

Hidaka, et al., "Differences in 20q13.2 Copy Number Between Colorectal Cancers with and without Liver Metastasis," Clinical Cancer Research, vol. 6, 2712-2717, Jul. 2000.

Hu, et al., "Increased Migration and Metastatic Potential of Tumor Cells Expressing Aquaporin Water Channels," FASEB J., 20, 1228-1236, 2006.

Hugh, et al., "Breast Cancer Subtypes and Response to Docetaxel in Node-Positive Breast Cancer: Use of an Immunohistochemical Definition in the BCIRG 001 Trial," Journal of Clinical Oncology, vol. 27, No. 8, Mar. 10, 2009.

Hyman, et al., "Impact of DNA Amplification on Gene Expression Patterns in Breast Cancer," Cancer Research, 62, 6240-6245, Nov. 1, 2002.

Irshad, et al., "The Brn-3b Transcription Factor Regulates the Growth, Behavior, and Invasiveness of Human Neuroblastoma Cells in Vitro and in Vivo," The Journal of Biological Chemistry, vol. 279, No. 20, 21617-21627, May 14, 2004.

Lee, et al., "Merlin, a Tumor Suppressor, Interacts with Transactivation-Responsive RNA-Binding Protein and Inhibits its Oncogenic Activity," The Journal of Biological Chemistry, vol. 279, No. 29, 30265-30273, Jul. 16, 2004.

Letessier, et al., "Frequency, Prognostic Impact, and Subtype Association of 8p12, 8q24, 11q13, 12p13, 17q12, and 20q13 Amplifications in Breast Cancer," BMC Cancer, 2006, 6:245.

Levenson, et al.l, "Resveratrol Acts as an Estrogen Receptor (ER) Agonist in Breast Cancer Cells Stably Trasfected with ERα," Int. J. Cancer, 104, 587-596 (2003).

Li et al., "Oncogene ZNF217 Amplifications on Chromosome 20 q in Ovarian Serous Cystadenocarcinoma and Its Clinical Implications," J. South Med Univ, 2006: 26(6).

Ma, et al., "A Two-Gene Expression Ratio Predicts Clinical Outcome in Breast Cancer Patients Treated with Tamoxifen," Cancer Cell, Jun. 2004, vol. 5.

MacKay, et al., "A High-Resolution Integrated Analysis of Genetic and Expression Profiles of Breast Cancer Cell Lines," Breast Cancer Res Treat, (2009), 118: 481-498.

Millar, et al., "Prediction of Local Recurrence, Distant Metastases, and Death After Breast-Conserving Therapy in Early-Stage Invasive Breast Cancer Using a Five-Biomarker Panel," Journal of Clinical Oncology, vol. 27, No. 28, Oct. 1, 2009.

Muraoka-Cook, et al., "Conditional Overexpression of Active Transforming Growth Factor β1 In vivo Accelerates Metastases of Transgenic Mammary Tumors," Cancer Res, 2004, 64: 9002-9011.

Nguyen, et al., "Breast Cancer Subtype Approximated by Estrogen Receptor, Progesterone Receptor, and HER-2 is Associated with Local and Distant Recurrence After Breast-Conserving Therapy," Journal of Clinical Oncology, vol. 26, No. 14, May 10, 2008.

Plevova, et al., "CCND1 and ZNF217 Gene Amplification is Equally Frequent in BRCA1 and BRCA2 Associated and Non-BRCA Breast Cancer," Neoplasma, 57, 4, 2010.

Pollack, et al., "Microarray Analysis Reveals a Major Direct Role of DNA Copy Number Alteration in the Transcriptional Program of Human Breast Tumors," PNAS, Oct. 1, 2002, vol. 99, No. 20, 12963-12968.

Soule, et al., "Isolation and Characterization of a Spontaneously Immortalized Human Breast Cancer Epithelial Cell Line, MCF-10," Cancer Res, 1990, 50: 6075-6086.

Tait, et al., "Ultrastructural and Immunocytochemical Characterization of an Immortalized Human Breast Cancer Epithelial Cell Line, MCF-10," Cancer Res, 1990, 50: 6087-6094.

Tanner, et al., "Amplification of Chromosomal Region 20q13 in Invasive Breast Cancer: Prognostic Implications," Clinical Cancer Research, vol. 1, 1455-1461, Dec. 1995.

Tanner, et al., "Frequent Amplification of Chromosomal Region 20q12-q13 in Ovarian Cancer," Clin Cancer Res, 2000, 6: 1833-1839.

Vendrell, et al., "Estrogen Regulation in Human Breast Cancer Cells of New Downstream Gene Targets Involved in Estrogen Metabolism, Cell Proliferation and Cell Transformation," Journal of Molecular Endocrinology, (2004) 32, 397-414.

Vendrell, et al., "Molecular Changes Associated with the Agonist Activity of Hydroxy-Tamoxifen and the Hyper-Response to Estradiol in Hydroxy-Tamoxifen-Resistant Breast Cancer Cell Lines," Endocrine-Related Cancer, (2005) 12, 75-92.

Vendrell, et al., "A Candidate Molecular Signature Associated with Tamoxifen Failure in Primary Breast Cancer," Breast Cancer Research, 2008, 10: R88.

Voduc, et al., "Breast Cancer Subtypes and the Risk of Local and Regional Relapse," Journal of Clinical Oncology, vol. 28, No. 10, Apr. 1, 2010.

Yilmaz, et al., "EMT, the Cytoskeleton, and Cancer Cell Invasion," Cancer Metastasis Rev, (2009) 28: 15-35.

\* cited by examiner

ZNF217 A NEW PROGNOSTIC AND PREDICTIVE BIOMARKER OF RECURRENT INVASIVE AND METASTATIC PHENOTYPES IN BREAST CANCER

RELATED APPLICATION DATA

This application is a National Stage Application under 35 U.S.C. 371 of co-pending PCT application PCT/EP2010/060381 designating the United States and filed Jul. 19, 2010; which claims the benefit of U.S. Provisional application No. 61/226,304 and filed Jul. 17, 2009 and EP patent application number 09165733.8 and filed Jul. 17, 2009 all of which are hereby incorporated by reference in their entireties.

The present invention relates to methods and kits for determining the prognosis of a breast cancer. The methods involve determining the level of expression of the ZNF217 gene in sample taken from a patient wherein over-expression of ZNF217 is correlated with likelihood of metastasis and with likelihood of relapse/recurrence of the cancer.

Cancer is a major health issue and kills millions of people worldwide every year. Diagnostic methods for cancer have improved and it is now often possible to diagnose cancers at early stages. In order for cancer treatments to be effective, accurate and simple methods for prognosis of cancer are required.

Cancer prognosis is often determined based on histological and clinical data such as tumor size, invasion, spread to lymph nodes or metastasis. However, this determination is often difficult to make in cancers which are diagnosed at early stages when clinical symptoms and histological data are not available or not evident.

Breast cancer markers such as ER alpha (ER) (detected by immunohistochemistry) and ERBB2/HER2 (detected by immunohistochemistry and/or FISH) have been classically used for cancer prognosis, and ER-negative and/or ERBB2/HER2-positive breast tumors are tumors with poor prognosis. However, ≈60-70% of breast cancers are ER+ and ERBB2/HER2+ breast cancers represent only ≈15-20% of all breast cancers. Thus there's an urgent need for new prognostic biomarkers either to add a new prognostic/predictive value to the biomarkers currently used or to predict the recurrence/relapse of the cancer, in particular in those breast cancers currently considered as "cancers with better prognostic" i.e. in ER-positive breast cancers, and in particular in ER-positive HER2-negative breast cancers.

Recently, immunohistological (ER, PR, HER2, KI67) and/or clinical (SBR) parameters have been proposed to classify breast cancers into subtypes that are biologically distinct and behave differently (Blows et al., 2010; Cheang et al., 2009; Hugh et al., 2009; Millar et al., 2009; Nguyen et al., 2008). The prognosis and chemotherapy sensitivity of the different molecular subgroups are different. Luminal-like cancers are ER+ and/or PR (Progesterone Receptor)-positive and therefore sensitive to endocrine therapy, and may have a more favourable prognosis than the HER2+ and Triple negative subtypes, even in the absence of any therapy. Luminal B subtype is equivalent to those that express either HER2 or that possess a high proliferative phenotype given by KI67 or SBR (that takes into account the number of mitoses observed) (Cheang et al., 2009; Hugh et al., 2009; Millar et al., 2009; Nguyen et al., 2008; Voduc et al., 2010). Luminal B breast cancers have been shown to have less favourable long-term survival than luminal A breast cancers (Blows et al., 2010; Cheang et al., 2009; Hugh et al., 2009; Nguyen et al., 2008; Voduc et al., 2010). Utmost importance is then attached to markers aimed at re-stratifying the luminal subclasses, in particular the luminal A subclass.

WO98/02539 describes genes from a region of amplification on chromosome 20 associated with cancers. The genes disclosed may be used as probes specific for the 20q13 amplicon for monitoring the relative copy of corresponding sequences in the genome of tumor cells. According to this document, the ZABC-1 gene (ZNF217 gene) maps to the core of the 20q13.2 amplicon and is over-expressed in primary tumors and breast cancer cell lines having 20q13.2 amplification. According to WO98/02539, the presence or absence and/or level of expression of 20q13 proteins can be indicative of the presence, absence, or extent of a cancer. However, in WO98/02539, expression levels of the ZABC-1 gene (ZNF217 gene) are not measured in tumor samples and shorter disease free survival is only correlated with high-level 20q13 amplification.

WO2006/065940 describes a new prognostic and therapeutic target, the HTPAP gene, which when amplified confers poor prognosis in breast cancer patients. Amplification of the HTPAP gene may be associated with the detection of other amplifications such as the ZNF217 amplicon.

Sun Guiqin et al. (2008) describes the influence of ZNF217 silencing on the biological behaviour of a human ovarian cancer cell line (Sun et al., 2008).

According to Li Jing et al. (2006) ZNF217 amplification is significantly associated with ovarian cancer (Li et al., 2006).

Quinlan et al. (2007) focuses on the evidence that ZNF217 is an oncogene which is amplified in various cancers (Quinlan et al., 2007).

Huang Guiqing et al. (2005) provides laboratory experiments showing that ZNF217 suppresses cell death associated with chemotherapy and telomere dysfunction (Huang et al., 2005).

WO03/079748 relates to potentiation of cancer therapies by ZNF217 inhibition.

High-level 20q13 amplifications are found in 6.8% (Tanner et al., 2000) 8% (Ginestier et al., 2006; Plevova et al., 2010) and 19% (Letessier et al., 2006) of breast cancers. However, since several studies have shown that the amplification level of a gene or a chromosomal region can have, in some cases, substantial impact on the gene(s) expression level in tumor samples, other mechanisms such as epigenetic, transcriptional or post-transcriptional mechanisms are also important events contributing to the gene expression. This is also true for amplification of ZNF217 and expression levels of ZNF217, as high ZNF217 expression levels could be observed in breast tumors and breast cell lines not possessing the amplification (Collins et al., 1998; Collins et al., 2001). Moreover, Mackay et al. (2009) did not find any significant correlation between ZNF217 expression and ZNF217 gene copy number (Mackay et al., 2009).

Further, it is not clear to what extend the 20q13 amplification is correlated with poor prognosis in breast cancer. Letessier et al. (2006) did not find any association between high-level 20q13 amplification and poor outcome in breast cancers (Letessier et al., 2006). Conversely, another study could observe the prognostic value of 20q13 amplification in breast cancer, but only with high-level 20q13 amplification and not with low/intermediate-level 20q13 amplification (Tanner et al., 1995). Strikingly, 20q13 amplification may be both associated with a good prognosis or a bad prognosis in breast cancer. Ginestier et al. (2006) observed two types of amplification. In the first type, the ZNF217 locus was amplified but amplification was not detected at two other loci of 20q13 (Ginestier et al., 2006). In the second type, the amplified region seemed larger and involved two or three loci among ZNF217, MYBL2 and STK6. The two types showed different gene expression profiles and were associated with different histoclinical features including lymph node status and survival. Tumors with amplification at two or three loci were associated with good prognosis, while tumors with amplification at ZNF217 only were more frequently associated with poor prognosis. Ginestier et al. further confirmed that there was no statistical correlation between the ZNF217 mRNA expression levels and the ZNF217 amplification in the ZNF217-only amplified tumors, and that ZNF217 mRNA expression levels were not able to discriminate these tumors from tumors without any amplification (Ginestier et al., 2006).

Finally, two studies found ZNF217 amplification associated with ER− and PR− negative status (Letessier et al., 2006; Plevova et al., 2010)

The prognostic value of ZNF217 amplification and of ZNF217 expression level in breast cancer has therefore remained largely unclear.

The present invention shows that expression level of ZNF217, independently of amplification of the ZNF217 gene, represents a new marker of poor prognosis in breast cancer patients prone to relapse and to develop metastases. More particularly, ZNF217 is a potent poor prognosis marker of breast cancers classified by the current available clinical markers/parameters as cancers with good/better prognosis (e.g. the ER+ subclass, the HER2− subclass, the luminal subclass (ER+ and/or PR+), the ER+/HER2− subclass, the SBR1 and/or SBR2 subclass, no/few lymph node invasion subclass (≤3), the ER+ and/or PR+ and SBR1 and/or SBR2 subclass, the ER+/HER2−/SBR1 and/or SBR2 subclass, the ER+/HER2−/SBR1 and/or SBR2/no/few lymph node invasion (≤3) subclass, the luminal A subclass). Assessing ZNF217 expression levels alone or in association with other prognostic markers thus allows the re-stratification of these cancers classified as having good/better prognosis into two subclasses: "good prognosis" breast cancers (with low ZNF217 expression levels) or "bad prognosis" breast cancers (with high ZNF217 expression levels), thus helping clinicians for therapeutic decision.

Surprisingly, ZNF217 has a higher prognostic value than other markers commonly used for cancer prognosis such as ERBB2/HER2 and ESR1/ER.

Patients classified as having a "good prognosis" by conventional techniques but with tumors expressing higher than normal levels of ZNF217 are therefore candidates for aggressive cancer therapy.

Moreover, as deregulated ZNF217 expression levels are associated with reduced response to endocrine therapy or to endocrine/chemotherapy, ZNF217 also represents a predictive marker for anti-cancer therapies, and in particular, for endocrine therapy.

The present invention shows that ZNF217 is a powerful tool for identifying in ER− positive or in ER-positive HER2− negative breast tumors, patients with aggressive tumors, with a poor prognosis for relapse-free survival and/or with a poor prognosis for overall survival. Thus, ZNF217 is a bad prognostic biomarker that possesses an added value compared to the actual bio markers of breast cancer, as ZNF217 allows the stratification of ER+ and/or PR+ breast tumor samples and ER+ and/or PR+/HER2− breast tumor samples. The ER-positive breast tumors are usually treated by endocrine therapy. Determination of the ZNF217 expression status provides useful information to clinicians to decide on the best course of treatment, as ER-positive HER2-negative ZNF217-positive tumors are more aggressive tumors prone to develop metastasis and/or to recur under therapy. These tumors are thus candidate for a more aggressive cancer therapy.

SUMMARY OF THE INVENTION

Figure 1:
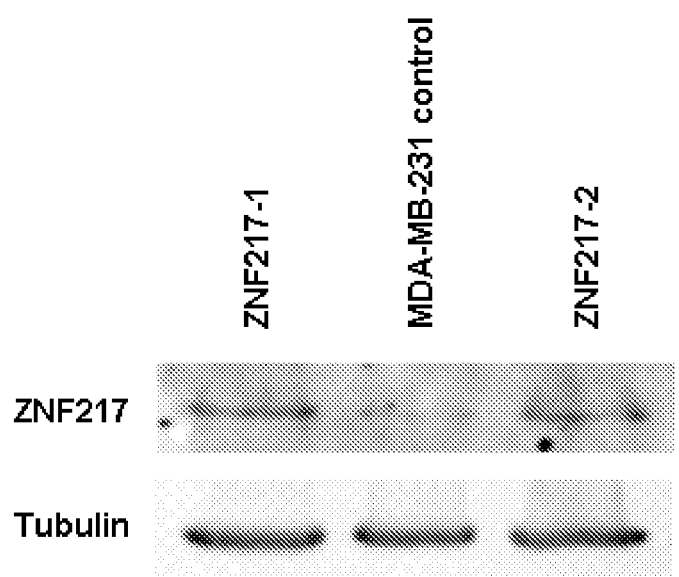
FIG. 1 are Western blots analyzing total protein extracts from cell lines with an anti-ZNF217 antibody.

The present invention relates to methods for determining the prognosis of a breast cancer in a patient, said breast cancer having a good prognosis as determined by conventional immunohistochemical and/or histological grading, comprising measuring the level of expression of the ZNF217 gene in a sample from said patient, and classifying the cancer as having a poor prognosis if the ZNF217 gene is over-expressed in said sample.

Preferably, the methods of the present invention allow re-stratification or re-classification of a patient having a "good" prognosis as determined by conventional methods. Preferably, said patient has been diagnosed with a breast cancer displaying at least one marker of good prognosis selected among ER+, PR+, HER2−, low proliferative index (given by SBR1 and SBR2 or given by low KI67), luminal subclass, luminal A subclass and lymph node status (no/few lymph nodes invaded, ≤3).

In the methods of the present invention, the cancer is classified or re-classified as prone to recur and/or prone to develop an invasive or metastatic phenotype if the ZNF217 gene is over-expressed in said sample.

In a first embodiment, the present invention is directed to methods for determining the prognosis of a breast cancer in a patient comprising the following steps:

Testing a sample previously taken from said patient for at least one prognostic marker of breast cancer and assessing the level of expression of the ZNF217 gene in said sample;

If the sample displays at least one marker classifying the breast cancer as having a favorable prognosis, re-classifying the breast cancer as having a poor prognosis if the ZNF217 gene is over-expressed in said sample.

In another embodiment, the present invention is directed to methods for determining the prognosis of a breast cancer patient in a patient comprising the following steps:

Testing a sample previously taken from said patient for at least one prognostic marker of breast cancer, Assessing the level of expression of the ZNF217 gene if the sample displays at least one marker classifying the breast cancer as having a favorable prognosis, Classifying the breast cancer as having a poor prognosis if the ZNF217 gene is over-expressed in said sample.

Preferably, said prognostic marker classifying the breast cancer as having a favorable prognosis is determined by a histological grading system and/or an immunohistochemical grading system and/or detection of ERBB2 amplification).

More preferably, said prognostic marker classifying the breast cancer as having a favorable prognosis is selected in the group consisting of ER+, PR+, HER2−, low proliferative index (given by SBR1 and SBR2 or given by low KI67), luminal subtype, luminal A subtype and lymph node status (no/few lymph node invaded ($\leq 3$)).

Even more preferred, said prognostic marker classifying the breast cancer as having a favorable prognosis classifies the breast cancer as having a subtype selected in the group consisting of the ER+ subclass, the HER2− subclass, the luminal subclass (ER+ and/or PR+), the ER+/HER2− subclass, the SBR1 and/or SBR2 subclass, no/few lymph node invasion subclass ($\leq 3$), the ER+ and/or PR+ and SBR1 and/or SBR2 subclass, the ER+/HER2−/SBR1 and/or SBR2 subclass, the ER+/HER2−/SBR1 and/or SBR2/no/few lymph node invasion ($\leq 3$) subclass, the luminal A subclass. SBR1 and/or SBR2 that sign low proliferative phenotype can be replaced by low KI67 in the corresponding subclasses.

Preferably, the cancer is re-classified as prone to recur and/or prone to develop an invasive or metastatic phenotype if the ZNF217 gene is over-expressed in said sample.

Preferably, the cancer is classified or re-classified as having a poor prognosis for relapse-free survival if the ZNF217 gene is over-expressed in said sample.

In other embodiments, the cancer is classified or re-classified as having a poor prognosis for overall survival if the ZNF217 gene is over-expressed in said sample.

In other embodiments, the cancer is classified or re-classified as having a poor prognosis under endocrine therapy if the ZNF217 gene is over-expressed in said sample.

In other embodiments, the cancer is classified or re-classified as having a poor prognosis under chemotherapy and/or endocrine therapy if the ZNF217 gene is over-expressed in said sample.

In other embodiments, the cancer is classified or re-classified as having a poor prognosis under endocrine therapy if the ZNF217 gene is over-expressed in said sample.

In other embodiments, the cancer is classified or re-classified as having a poor prognosis under chemotherapy if the ZNF217 gene is over-expressed in said sample.

In the methods of the present invention, the level of expression of the ZNF217 gene is preferably compared to a control sample.

In some embodiments, the control sample is the median level of expression of the ZNF217 gene observed in a healthy population.

Advantageously, the control sample is the median level of expression of ZNF217 in samples taken from patients having breast cancers. Preferably, the sample is a breast tumor sample.

The present invention is also directed to methods for re-stratification of breast cancer patients having a good prognosis as determined by immunohistochemistry and/or detection of ERBB2 amplification and/or histological grading, comprising measuring the level of expression of the ZNF217 gene in a sample from at least one patient, and re-classifying the patient as having a poor prognosis if the ZNF217 gene is over-expressed in said sample.

Preferably, the breast cancer patients have at least one marker of good prognosis selected among ER+, PR+, HER2−, SBR1 and/or SBR2, low KI67, luminal subclass, luminal A subclass and lymph node status ($\leq 3$).

Preferably, the methods of the present invention comprise measuring the level of expression of the ZNF217 gene in a sample by quantification of the mRNA of the ZNF217 gene.

Preferably, the methods of the present invention comprise measuring the level of expression of the ZNF217 gene in a sample by quantification of the polypeptide(s) encoded by the ZNF217 gene.

DETAILED DESCRIPTION OF THE INVENTION

The present invention is based on the observation that the level of expression of the ZNF217 gene is a remarkable prognostic marker for breast cancer. More particularly, ZNF217 has a high prognostic value in breast cancer patients which have previously been classified as having a "favorable" or "good" prognosis by conventional techniques. ZNF217 is a potent poor prognosis marker for breast cancers classified by the current available clinical markers/indicators as cancers with good/better prognosis (e.g. the ER+ subclass, the HER2− subclass, the luminal subclass (ER+ and/or PR+), the ER+/HER2-subclass, the SBR1 and/or SBR2 subclass, no/few lymph node invasion subclass ($\leq 3$), the ER+ and/or PR+ and SBR1 and/or SBR2 subclass, the ER+/HER2−/SBR1 and/or SBR2 subclass, the ER+/HER2−/SBR1 and/or SBR2/no/few lymph node invasion ($\leq 3$) subclass, the luminal A subclass. SBR1 and/or SBR2 that sign low proliferative phenotype can be replaced by low KI67 in the corresponding subclasses). Assessing ZNF217 expression levels alone or in association with other prognostic markers thus provides for re-stratification of these cancers classified as having good/better prognosis into two subclasses: "good prognosis" breast cancers (with low ZNF217 expression levels) or "bad prognosis" breast cancers (with high ZNF217 expression levels), thus providing helpful information to clinicians. Surprisingly, ZNF217 has a higher prognostic value than other markers commonly used for cancer prognosis such as ERBB2/HER2 and ESR1/ER.

Over-expression or high expression levels of ZNF217 are characteristic of breast tumors having an invasive or metastatic phenotype, with a poor prognosis for relapse-free survival and/or with a poor prognosis for overall survival. Overexpression of this gene in breast cancer cells is statistically significantly correlated with increased disease recurrence and worse prognosis.

The present invention relates to a method for identifying a breast cancer and/or a breast tumor prone to recur and/or a breast cancer and/or a breast tumor having or prone to develop an invasive or metastatic phenotype. More specifically, the present invention relates to a method for identifying a breast cancer and/or a breast tumor prone to recur and/or a breast cancer and/or a breast tumor having or prone to develop an invasive or metastatic phenotype wherein the breast cancer or the breast tumor has previously been classified as having a favorable prognosis by conventional techniques.

"Cancer" refers to diseases in which a group of cells displays uncontrolled growth/division, invasion and sometimes metastasis.

"Statistically significant" preferably refers to a correlation or an association at a confidence level of at least 95% ($p<0.05$).

The terms "invasive" or "aggressive" refer to a cancer or to a quickly growing tumor having a tendency to extend beyond its boundaries into adjacent tissues.

The term "metastatic" refers to the spread of a cancer or tumor from the organ of origin to additional organs/distal sites in the patient.

In preferred embodiments, the present invention relates to methods for determining the prognosis of a breast cancer in a patient, said breast cancer having a "good" prognosis as determined by immunohistochemistry and/or detection of ERBB2 amplification and/or histological grading, comprising measuring the level of expression of the ZNF217 gene in a sample from said patient, and classifying or re-classifying the cancer as having a poor prognosis if the ZNF217 gene is over-expressed in said sample.

In a first embodiment, the present invention is directed to methods for determining the prognosis of a breast cancer in a patient comprising the following steps:

Testing a sample previously taken from said patient for at least one prognostic marker of breast cancer and assessing the level of expression of the ZNF217 gene in said sample;

If the sample displays at least one marker classifying the breast cancer as having a favorable prognosis, re-classifying the breast cancer as having a poor prognosis if the ZNF217 gene is over-expressed in said sample.

The sample may be tested simultaneously for at least one conventional prognostic marker and for ZNF217 expression level. The prognostic marker(s) and the ZNF217 expression level may also be assessed successively and independently.

In another embodiment, the present invention is directed to methods for determining the prognosis of a breast cancer in a patient comprising the following steps:

Testing a sample previously taken from said patient for at least one prognostic marker of breast cancer, Assessing the level of expression of the ZNF217 gene if the sample displays at least one marker classifying the breast cancer as having a favorable prognosis, Classifying the breast cancer as having a poor prognosis if the ZNF217 gene is over-expressed in said sample.

The prognostic value of ZNF217 expression level is enhanced for breast cancers having a favorable prognosis as determined by conventional methods.

A number of breast cancer patients having a "good" prognosis as determined by conventional methods still develop an invasive, metastatic cancer or have shortened relapse-free survival or have a shortened overall survival rate. Measuring the level of expression of the ZNF217 gene provides for re-stratification or re-classification of these patients previously classified as having a "good" prognosis into two subclasses: "good prognosis" breast cancers (with low ZNF217 expression levels) or "bad prognosis" breast cancers (with high ZNF217 expression levels).

The terms "good prognosis" or "favorable" prognosis refer to patients having a better prognosis than patients without one or several given marker(s) of a good prognosis and/or patients with a or several given marker(s) of bad prognosis.

The term "marker" refers to an indicator which could provide a prognosis for a breast cancer. Sub-typing and sub-classification of breast cancer tumors is usually performed with a combination of markers. These markers classify breast cancers into different subtypes or subclasses.

Immunohistochemistry and/or detection of ERBB2 amplification and histological grading have been classically used to determine the prognosis of breast cancers in order to determine the most effective course of treatment for breast cancer patients.

Preferably, the methods of the present invention provide for re-stratification or re-classification of a patient having a "good" prognosis as determined by conventional methods such as immunohistochemistry and/or detection of ERBB2 amplification and histological grading.

The malignancy of infiltrating breast cancer may for example be scored according to any appropriate histological grading system. The majority of tumor grading systems currently employed for breast cancer combine nuclear grade, tubule formation and mitotic rate. One of the most common grading systems used is the Scarff-Bloom-Richardson (SBR) system (Bloom and Richardson, 1957). The SBR grade or histological grade corresponds to the addition of the tumor tubule formation score, plus the number of mitoses score, plus the nuclear pleomorphism score. The combined score is then converted to the following SBR grade: SBR1 corresponding to low grade, SBR2 corresponding to intermediate grade, SBR3 corresponding to high grade.

The methods of the present invention provide for re-stratification of breast cancer patients having a favorable SBR grade. Among these patients previously classified as having a "good prognosis", high expression levels of ZNF217 is a marker for a bad prognosis.

Other conventional markers are receptor status based on the presence or absence of the estrogen receptor (ER), the progesterone receptor (PR) and/or the human epidermal growth factor receptor 2 (HER2/ErbB-2). Generally, ER+, PR+ and/or HER2− breast cancers are classified as having a "better"/"good" prognosis. Receptor status may classically be determined by immunohistochemistry and/or detection of ERBB2 amplification according to well known methods. Detection of ERBB2 amplification is usually carried out by FISH (fluorescence in situ hybridization).

Breast cancers of the ER+ and/or HER2− subclass are considered as having a "favorable" prognosis although a number of these patients will experience a recurrence of their breast cancer. In the methods of the present invention, a more precise classification or re-stratification of these patients/breast tumors is performed by assessing the expression level of the ZNF217 gene.

Other subtypes of breast cancer classically considered as having a "good" prognosis, are the luminal and the luminal A subtypes. Luminal-like cancers are ER+ and/or PR+ breast cancers. Luminal A breast cancers are those that are ER+ and/or PR+, HER2− and which have a low proliferative index (given by low KI67 or given by SBR1 and SBR2) (Cheang et al., 2009; Hugh et al., 2009; Voduc et al., 2010). Luminal A breast cancers can also be breast cancers with ER+ and/or PR+ and HER2− status (Millar et al., 2009; Nguyen et al., 2008) or breast cancers with ER+ and/or PR+ and low proliferative index (given by low KI67 or given by SBR1 and SBR2) (Voduc et al., 2010). Luminal B breast cancers are those cancers that possess ER+ and/or PR+ and also possess HER2+ or high proliferative index (high KI67 or SBR3) status (Cheang et al., 2009; Hugh et al., 2009). Luminal B breast cancers can also be those with ER+ and/or PR+ and HER2+ only (Millar et al., 2009; Nguyen et al., 2008).

In the methods of the present invention breast tumors of the luminal and/or the luminal A subtype are re-stratified or re-classified by assessing the level of expression of the ZNF217 gene.

Another well-known prognostic indicator in breast cancer is the lymph node status. Patients suffering from breast cancers with no or few invaded lymph nodes (≤3) are conventionally classified as having a favorable prognosis.

In the methods of the present invention, assessing the level of expression of the ZNF217 gene also provides for re-stratification of breast tumor subtypes combining several "good" prognosis markers such as the ER+ subclass, the HER2− subclass, the luminal subclass (ER+ and/or PR+), the ER+/HER2− subclass, the SBR1 and/or SBR2 subclass, no/few lymph node invasion subclass (≤3), the ER+ and/or PR+ and SBR1 and/or SBR2 subclass, the ER+/HER2−/SBR1 and/or SBR2 subclass, the ER+/HER2−/SBR1 and/or SBR2/no/few lymph node invasion (≤3) subclass, the luminal A subclass. SBR1 and/or SBR2 that sign low proliferative phenotype can be replaced by low KI67 in the corresponding subclasses.

In the methods of the present invention, breasts cancers having at least one classical indicator of a favorable prognosis are re-classified or re-stratified as prone to recur and/or prone to develop an invasive or metastatic phenotype if the ZNF217 gene is over-expressed in said sample.

In some embodiments, the breast cancers are re-classified or re-stratified as having a poor prognosis for relapse-free survival if the ZNF217 gene is over-expressed in said sample.

In other embodiments, the breast cancers are re-classified or re-stratified as having a poor prognosis for overall survival rate if the ZNF217 gene is over-expressed in said sample.

In other embodiments, the cancer is classified as having a poor prognosis under endocrine therapy if the ZNF217 gene is over-expressed in said sample. Seventy percent of breast cancer patients are positive for estrogen receptor alpha (ERα) and therefore suitable for endocrine therapy, a strategy which aims to block the mitogenic effects of estrogen on breast cancer cells. Different molecules are used in endocrine therapy: the selective estrogen receptor modulators (SERM) such as tamoxifen, that prevents the binding of estrogen to its receptor; the selective estrogen receptor down-regulators (SERD) such as fulvestrant (ICI 182,780), an ER antagonist that also induces destabilization and degradation of the receptor; the aromatase inhibitors (such as exemestane, letrozole, anastrozole) that, by blocking the aromase activity, inhibit the conversion of androgens into estrogens.

Expression levels of ZNF217 therefore also have a predictive value. ZNF217 expression levels are correlated with metastasis and aggressive breast cancer in patients under endocrine therapy.

In other embodiments, expression levels of ZNF217 therefore also have a predictive value. ZNF217 expression levels are correlated with metastasis and aggressive breast cancer in patients under endocrine therapy and/or chemotherapy.

In the methods of the present invention, the level of expression of the ZNF217 gene is preferably compared to a control sample.

In some embodiments, the control sample is the median level of expression of the ZNF217 gene observed in a healthy population.

More advantageously, the control sample is the median level of expression of ZNF217 in samples taken from patients having breast cancers and more preferably in breast tumor samples.

The present invention is also directed to methods for re-stratification of breast cancer patients having a good prognosis as determined by immunohistochemistry and/or detection of ERBB2 amplification and/or histological grading, comprising measuring the level of expression of the ZNF217 gene in a sample from at least one patient, and re-classifying the patient as having a poor prognosis if the ZNF217 gene is over-expressed in said sample.

Preferably, the methods of the present invention comprise measuring the level of expression of the ZNF217 gene in a sample by quantification of the mRNA of the ZNF217 gene.

In other embodiments, the methods of the present invention comprise measuring the level of expression of the ZNF217 gene in a sample by quantification of the polypeptide(s) encoded by the ZNF217 gene.

The present invention demonstrates high levels of expression or over-expression of ZNF217 in the primary breast tumors of patients prone to relapse and/or to develop metastases. Interestingly, the prognostic value of ZNF217 expression is higher than the prognostic value of other prognostic markers for breast cancer such as ERBB2/HER2 and ESR1/ER.

A "prognosis" is the likely course and outcome of a disease. The prognosis may include the likelihood of complications of the cancer, of metastasis, of spread, probable outcome of the cancer, likelihood of recovery, overall survival rate and/or overall death rate. Preferably, it is the probability that a patient will recover or have a recurrence/relapse of the cancer. This information is useful to the patient but also to the physician and/or clinician in determining the most effective course of treatment. A determination of the likelihood for a cancer relapse or of the likelihood of metastasis can assist the physician and/or clinician in determining whether a more conservative or a more radical approach to therapy should be taken. Prognosis provides for selection and classification of patients who are predicted to benefit from a given therapeutic regimen.

The methods of the present invention provide prognosis for a breast cancer after it has been diagnosed and/or during therapeutic treatment of a cancer in particular under endocrine therapy.

In the methods of the present invention over-expression of the ZNF217 gene is correlated with a poor/worse prognosis for relapse-free survival.

In one embodiment, poor prognosis is that a cancer patient having a higher level of expression of the ZNF217 gene has a higher probability to develop a cancer recurrence or relapse than a patient having the same cancer without over-expression of ZNF217.

A higher level of expression of the ZNF217 gene in a sample from the patient is correlated with a higher probability for relapse or recurrence of the cancer in the patient compared to a patient having the same cancer without over-expression of ZNF217.

Preferably, a poor prognosis is a that a cancer patient has at least a 30%, 40%, 50%, 60%, 70%, 80% or more chance that the cancer will relapse in 1, 2, 3, 4, 5, 6, 7, 8, 9, 10 or more years from the date when the sample was taken. In some embodiments, there is a 30% chance or more that the cancer will relapse within 10 years.

Relapse-free survival (RFS) is defined as the percentage of patients who did not relapse after diagnosis of a primary breast cancer. In this case, the Kaplan-Meier curve simply represents the x % of patients who did not relapse after y amount of time.

In another embodiment, poor prognosis is that a cancer patient having a higher level of expression of the ZNF217 gene has a lower overall survival rate than a patient having the same cancer without over-expression of ZNF217.

A higher level of expression of the ZNF217 gene in a sample from the patient is correlated with a higher probability that the cancer will be fatal for the patient compared to a patient having the same cancer without over-expression of ZNF217.

Preferably, a poor prognosis is a that a cancer patient has at least a 30%, 40%, 50%, 60%, 70%, 80% or more chance that the cancer will be fatal within 1, 2, 3, 4, 5, 6, 7, 8, 9, 10 or more years from the date when the sample was taken. In some embodiments, there is a 30% chance or more that the cancer will be fatal within 5 years.

Overall survival (OS) is defined as the percentage of patients who survive after diagnosis of a primary breast cancer. In this case, the Kaplan-Meier curve simply represents the x % of patients survived after y amount of time.

The present invention also relates to methods of providing a prediction of development of metastases, a prognosis of relapse-free survival (RFS) or a prognosis of overall survival rate (OS) in a breast cancer patient comprising:
a) Obtaining a sample from said patient,
b) Measuring the level of expression of ZNF217 in said sample,
c) Predicting likelihood of occurrence of metastasis, RFS or OS based upon the measured level of ZNF217 wherein, when said level of ZNF217 is increased as compared to a control or normal sample, said likelihood of occurrence of metastasis is increased, said RFS is decreased or said OS is decreased.

The present invention also relates to methods of providing a prediction of development of metastases, a prognosis of relapse-free survival (RFS) or a prognosis of overall survival rate (OS) in a breast cancer patient comprising:
a) Obtaining a sample from said patient,
b) Testing said sample for conventional breast cancers prognostic markers,
c) If the sample has at least one marker or a combination of markers of "good" prognosis, assessing the level of expression of the ZNF217 gene in said sample,
d) Predicting likelihood of occurrence of metastasis, RFS or OS based upon the measured level of ZNF217 wherein, when said expression level of ZNF217 is increased as compared to a control or normal sample, said likelihood of occurrence of metastasis is increased, said RFS is decreased or said OS is decreased.

The present invention also relates to methods of providing a prediction of development of metastases, a prognosis of relapse-free survival (RFS) or a prognosis of overall survival rate (OS) in a breast cancer patient comprising:
a) Obtaining a sample from said patient,
b) Testing said sample for conventional breast cancers prognostic markers and assessing the level of expression of the ZNF217 gene,
c) If the sample has at least one marker or a combination of markers of "good" prognosis, assessing the level of expression of the ZNF217 gene in said sample, predicting likelihood of occurrence of metastasis, RFS or OS based upon the measured level of ZNF217 wherein, when said level of ZNF217 is increased as compared to a control or normal sample, said likelihood of occurrence of metastasis is increased, said RFS is decreased or said OS is decreased.

The methods of the present invention comprise measuring the level of expression of the ZNF217 gene in a sample from a patient.

Preferably, the methods of the present invention are in vitro methods. The methods of the present invention are carried out on a biological sample previously taken from a patient. Typically, the patient has been diagnosed with breast cancer.

The term "sample" refers to any biological sample obtained/taken from a patient including a blood sample, a plasma sample, a tissue sample, a cell sample or a tumor sample. Typically, the sample contains cancer or tumors cells such as for example breast cancer cells. In preferred embodiments, the sample is a breast tumor sample previously taken from a patient.

The methods of the invention include detecting or measuring the level of expression of the ZNF217 gene. The ZNF217 gene is a candidate oncogene on 20q13.2 first described by Collins et al. (Collins et al., 1998). The GENBANK accession number for the ZNF217 gene is NC_000020.10 (RefSeq: NM_006526.2).

The term "expression" may refer to measuring the level of transcription and/or the level of translation of the gene. In a first embodiment, the methods of the present invention comprise measuring the level of expression of the ZNF217 gene in a sample by quantification of the ZNF217 gene transcript(s) (mRNA). In another embodiment, the methods of the present invention comprise measuring the level of expression of the ZNF217 gene in a sample by quantification of the polypeptide(s) encoded by the ZNF217 gene.

In other embodiments, the amount of ZNF217 mRNA may be assessed indirectly by the measurement of a non-coding RNA (such as miRNA) that regulates gene expression. MicroRNAs (miRNAs) are post-transcriptional regulators that bind to complementary sequences in the 3' untranslated regions (3' UTRs) of target messenger RNA transcripts (mRNAs), usually resulting in gene silencing. miRNAs are short ribonucleic acid (RNA) molecules, on average only 22 nucleotides long. The human genome may encode over 1000 miRNAs, which may target about 60% of mammalian genes and are abundant in many human cell types. Each miRNA may repress hundreds of mRNAs. MiRNAs are well conserved in eukaryotic organisms and are thought to be a vital and evolutionarily ancient component of genetic regulation. Since then, miRNA research has revealed multiple roles in negative regulation (transcript degradation and sequestering, translational suppression) and possible involvement in positive regulation (transcriptional and translational activation). By affecting gene regulation, miRNAs are likely to be involved in most biologic processes. Aberrant expression of miRNAs has been implicated in numerous disease states, and miRNA-based therapies are under investigation. Several miRNAs have been found to have links with some types of cancer.

Expression levels of the ZNF217 gene are determined by any of a variety of methods known to the skilled person.

mRNA or transcripts of the ZNF217 gene are for example quantified by hybridization or reverse transcription and amplification (RT-PCR) followed by quantitative detection of the product by any known method. Any quantitative amplification method may be used in the methods of the present invention. Preferably, quantitative RT-PCR is carried out with the primer of SEQ ID NO. 1 (5'-AGTCCAAATCCCTGC-CATCT-3') and the primer of SEQ ID NO. 2 (5'-GGGGAAA-CACTGGTTTTAGG-3').

ZNF217 polypeptide(s) are for example quantified by immunoblotting, ELISA, mass spectrometry or binding assays. Preferably, ZNF217 polypeptide levels are measured in a binding assay with an or several anti-ZNF217 antibody(ies).

Preferably, the methods of the present invention include detecting a level of expression of the ZNF217 gene in a sample of tumor cells or cancer cells from a patient and comparing this level of expression to a control level of expression or to the level of expression in a control sample. The aggressiveness and prognosis of the cancer/tumor is determined on the basis of whether the expression of ZNF217 in the cancer/tumor is higher than in the control.

The term "over-expression" refers to a level of expression which is statistically significantly higher than the level of expression detected in the control sample.

The level of expression of ZNF217 is identified as being "over-expressed" or "higher" than the control if the expression level is at least 10%, 25%, 50%, 75%, 100% or more higher than the level of expression detected in the control sample.

The control may be a "normal" control sample meaning a non-tumor cell control sample or a non-cancerous cell control sample. The control sample can be an autologous control sample obtained from the patient. In that case the sample is obtained from the same patient from which the sample to be evaluated is obtained. The control sample is preferably from the same cell type or from the same organ. The control sample can be a normal control sample obtained from an individual who does not have cancer.

The normal control sample can also be a standard sample that contains the same amount of ZNF217 that is normally found in biological samples.

The normal control sample can also be a median level of expression of ZNF217 in samples taken from at least 5, 10, 15, 20 or more, different patients with the breast cancer or with the same subtype of breast cancer. The control samples are preferably collected from a Tissue Bank or a Ressources Biological Center where the complete clinical, histological, and biological information of the patient is available.

The cancer is classified or re-classified as a breast cancer prone to recur and/or as a breast cancer having or prone to develop an invasive or metastatic phenotype if the ZNF217 gene is over-expressed in the sample to be evaluated in comparison with the control sample.

The invention is also directed to kits for identifying a breast cancer prone to recur and/or a cancer having or prone to develop an invasive or metastatic phenotype comprising primers and/or probes derived from the ZNF217 gene and a control sample for the level of expression of the ZNF217 gene.

The invention also relates to kits for identifying a tumor prone to recur and/or a tumor having or prone to develop an invasive or metastatic phenotype comprising anti-ZNF217 antibodies and a control sample for the level of expression of the ZNF217 gene.

The kits may also comprise a positive control, a negative control and any reagents or any devices required to carry out the methods of the invention.

The methods and kits of the present invention may also comprise an "invariant" control which can be the level of expression of an housekeeping gene.

The invention also encompasses the use of such kits for carrying out the methods of the present invention and in particular to identify a cancer prone to recur and/or a cancer having or prone to develop an invasive or metastatic phenotype or to determine the prognosis of a cancer.

FIGURES

FIG. 1: Over-expression of ZNF217 in MDA-MB-231 breast cancer cells. Total protein extracts from cell lines were analyzed by Western blotting with an anti-ZNF217 antibody. Expression of $\alpha$-tubulin was used as an invariant control.

Figure 2A:
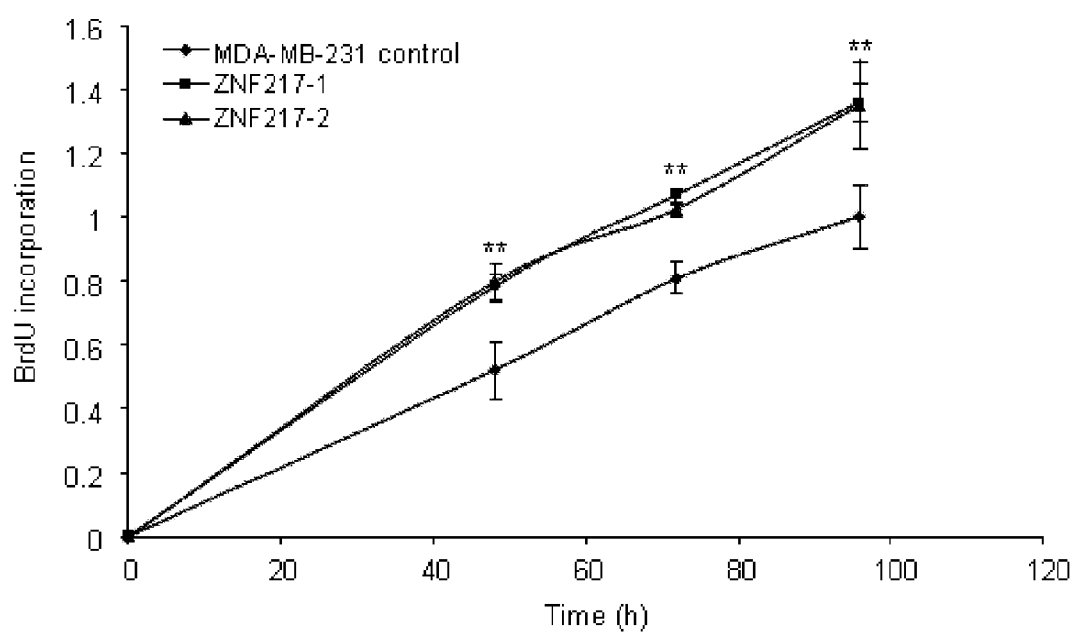
FIG. 2A is a graph showing impact of ZNF217 over-expression on cell proliferation and on cyclin expression levels in MDA-MB-231 cells.

FIG. 2: Impact of ZNF217 over-expression on cell proliferation and on cyclin expression levels in MDA-MB-231 cells. (A) The proliferating cells were analyzed using a BrdU labeling kit as described in the Material and methods section. Results are expressed as means±s.d. (standard deviation) from three independent experiments. **$P<0.01$ versus the corresponding MDA-MB-231 control cells according to Student's t-test. (B) Western blot analysis of cyclin A2, cyclin D1 and cyclin E2 protein expression levels in ZNF-217-transfected MDA-MB-231 cells. Expression of $\alpha$-tubulin was used as an invariant control.

Figure 3A:
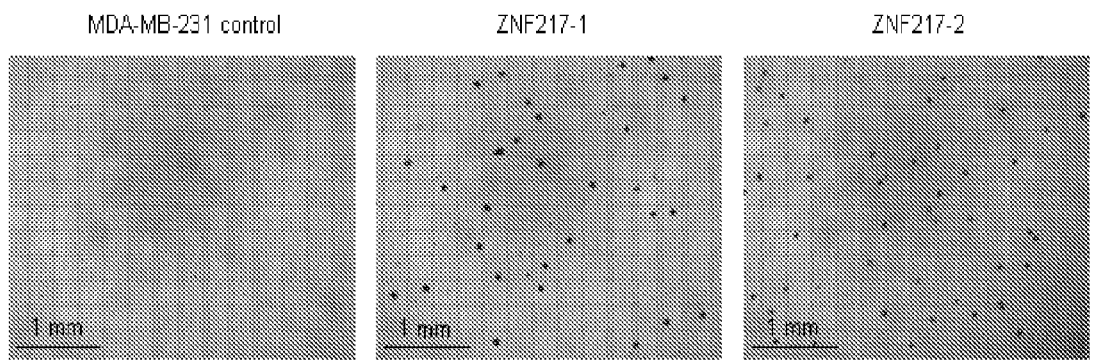
FIG. 3A is a photomicrograph of MDA-MB-231 control, ZNF217-1 and ZNF217-2 cells.
Figure 3B:
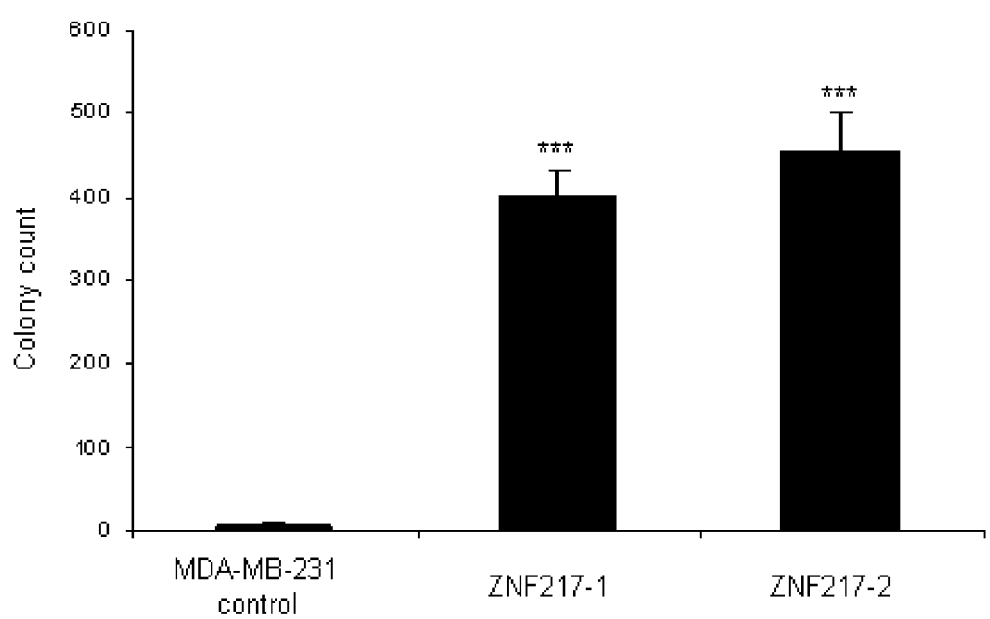
FIG. 3B is a graph of colony count versus cell type.

FIG. 3: Over-expression of ZNF217 in MDA-MB-231 cells increases their ability to form colonies in soft agar. MDA-MB-231 control, ZNF217-1 and ZNF217-2 cells were plated in 6-well plates in 10% FCS-DMEM with 0.45% agar (10,000 cells/well). Photomicrographs (pictures (A) and counting (B)) were taken 20 days after plating. Results are expressed as means±s.d. from at least three independent experiments. ***$P<0.001$ versus the corresponding MDA-MB-231 controls according to Student's t-test. All images were taken at ×1.25 magnification.

Figure 4:
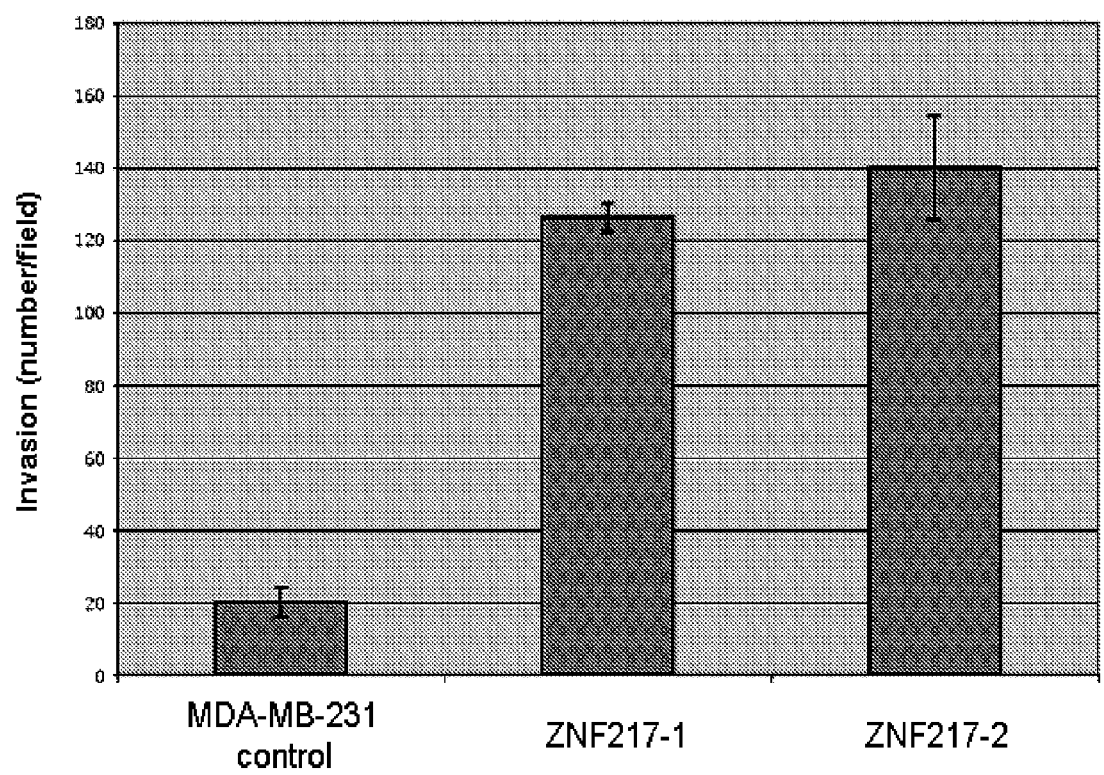
FIG. 4 is a graph of invasion number versus cell type.

FIG. 4: Boyden chamber invasion assay. The quantification of control, ZNF217-1 and ZNF217-2 cell invasion was carried out in Transwell cell culture chambers containing fluorescence-blocking porous polycarbonate membrane inserts. Cells that had invaded through the Matrigel were detected on the lower side of the filter by fluorescence and counted. The whole surface of the filter was counted and each assay was performed twice in triplicate for each condition. Results are expressed as means±s.d.

Figure 5A:
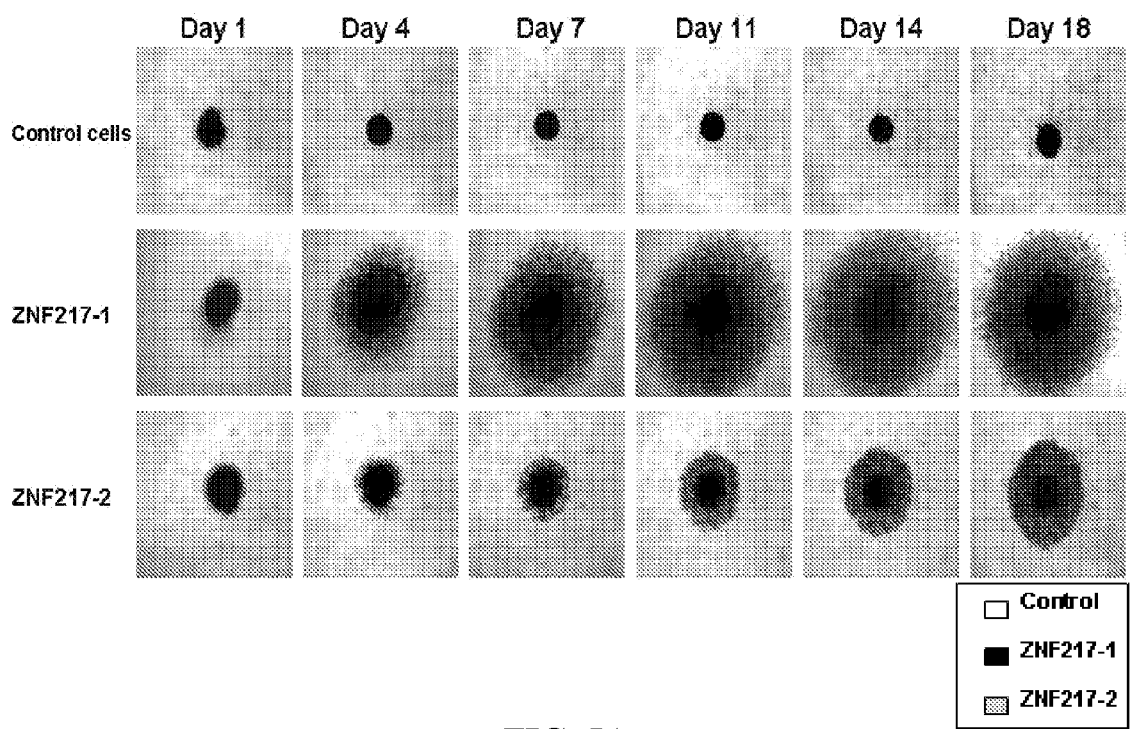
FIG. 5A are images of cell invasion.
Figure 5B:
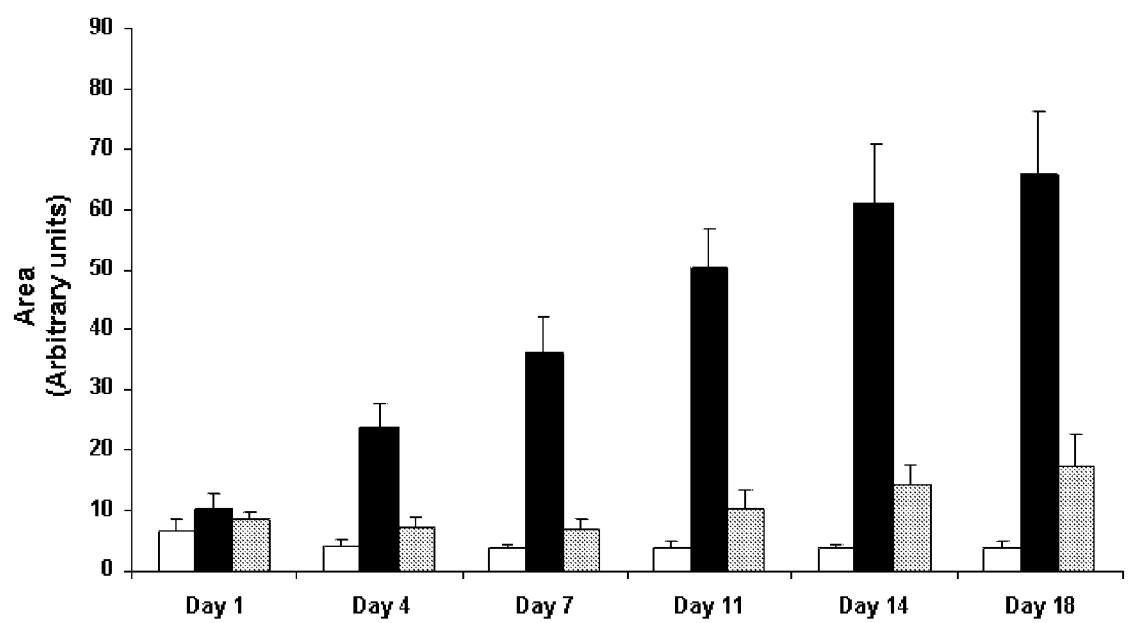
FIG. 5B is a graph of invasion area for each cell type.

FIG. 5: Control, ZNF217-1 and ZNF217-2 cell invasion culture assay. (A) Representative images from at least three independent experiments after 1, 4, 7, 11, 14 and 18 days of culture in Matrigel. All images were taken at ×1.5 magnification. (B) Matrigel invasion area of control (white bars), ZNF217-1 (black bars) and ZNF217-2 (grey bars) cells was measured using ImageJ software. Results are expressed as means±s.d. from at least three independent experiments. $P<0.01$ and *$P<0.001$ according to Student's t-test.

Figure 6:
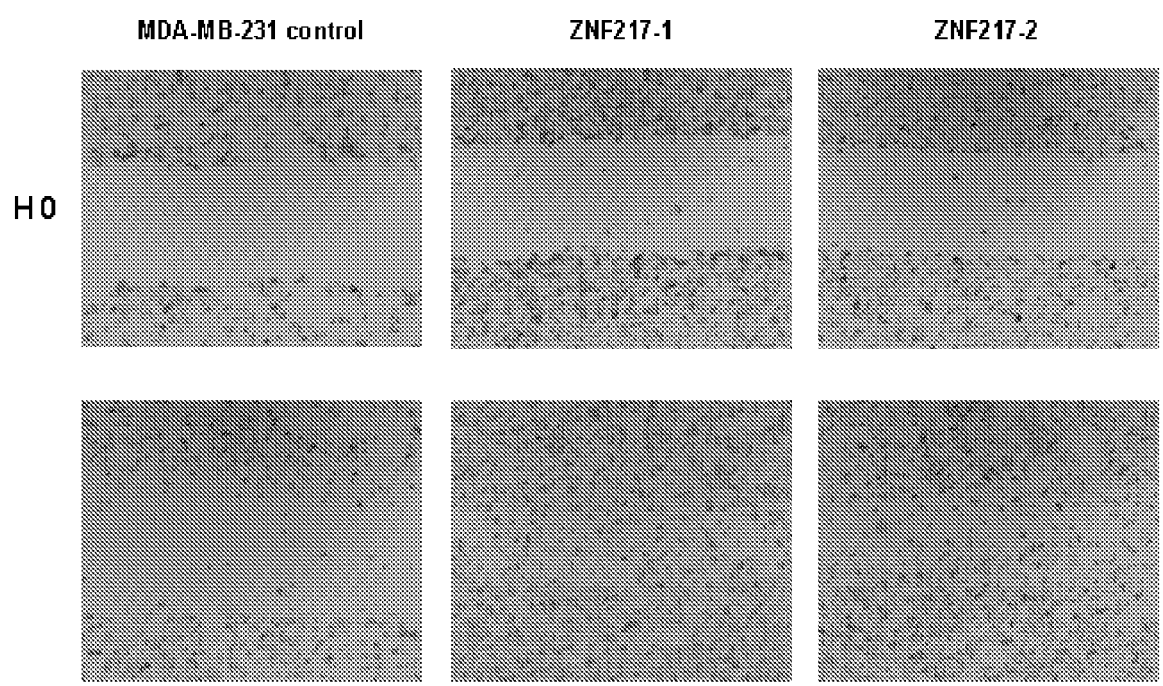
FIG. 6 are images of cell migration.

FIG. 6: ZNF217 promotes breast cancer cell migration (wound healing) Confluent monolayer of control or of ZNF217-over-expressing MDA-MB-231 cells was wounded by scratching and photographed at 0 hour (H 0), 26 hours (H 26). Images are representative of at least three independent experiments and were taken at ×2.5 magnification.

Figure 7A:
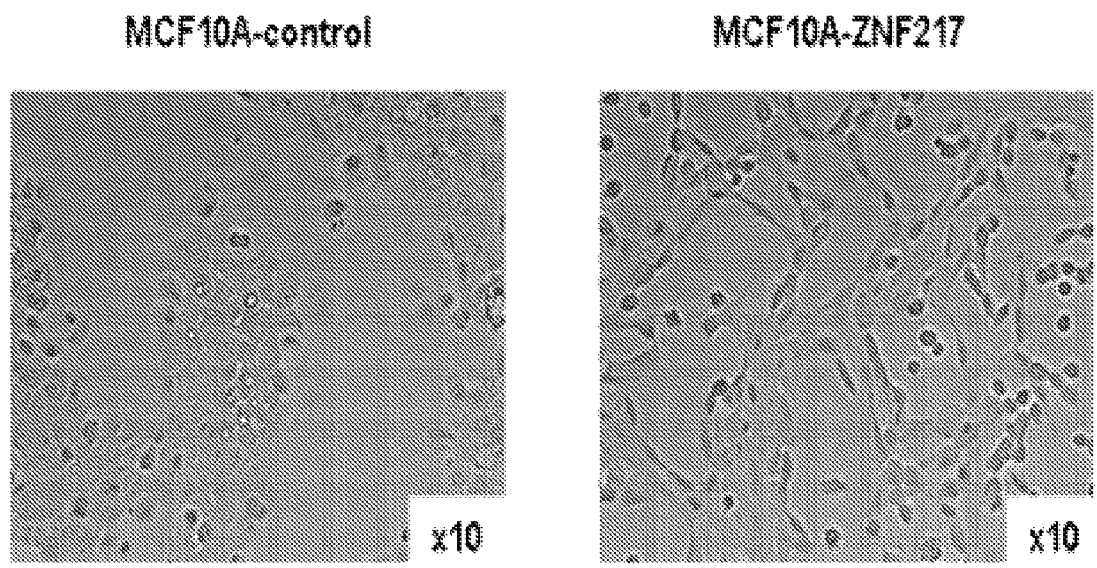
FIG. 7A are images of MCF 10A-control and MCF 10A-ZNF217 cell morphology at x10 magnification.
Figure 7B:
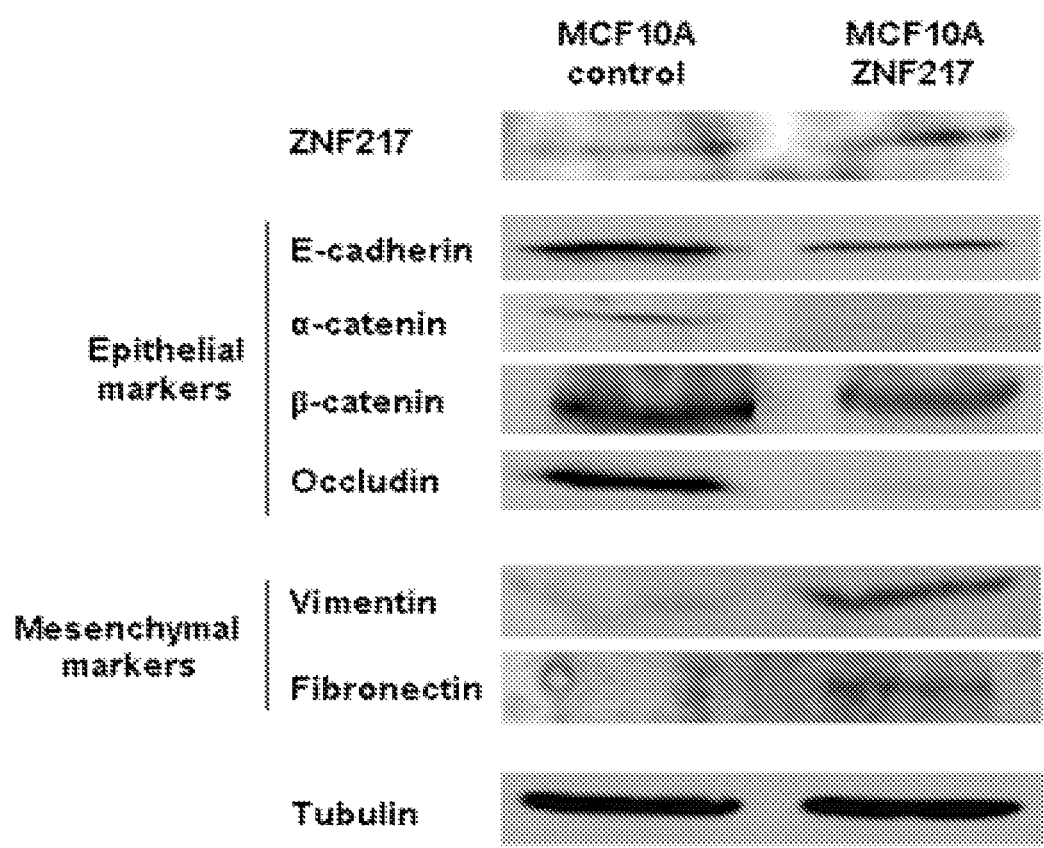
FIG. 7B are Western blots analyzing ZNF217, epithelial markers (E-cadherin, α-catenin, β-catenin and occludin) and mesenchymal markers (vimentin and fibronectin) using specific antibodies.

FIG. 7: ZNF217 induces EMT in epithelial breast MCF10A cells. (A) Representative images of MCF10A-control and MCF10A-ZNF217 cell morphology at ×10 magnification. (B) Western blot analysis of ZNF217, epithelial markers (E-cadherin, $\alpha$-catenin, $\beta$-catenin and occludin) and mesenchymal markers (vimentin and fibronectin) using specific antibodies as described in the Materials and methods section. Expression of $\alpha$-tubulin was measured as an invariant control. The Western blots shown are from one representative experiment of at least three independent experiments and cell lysates.

Figure 8A:
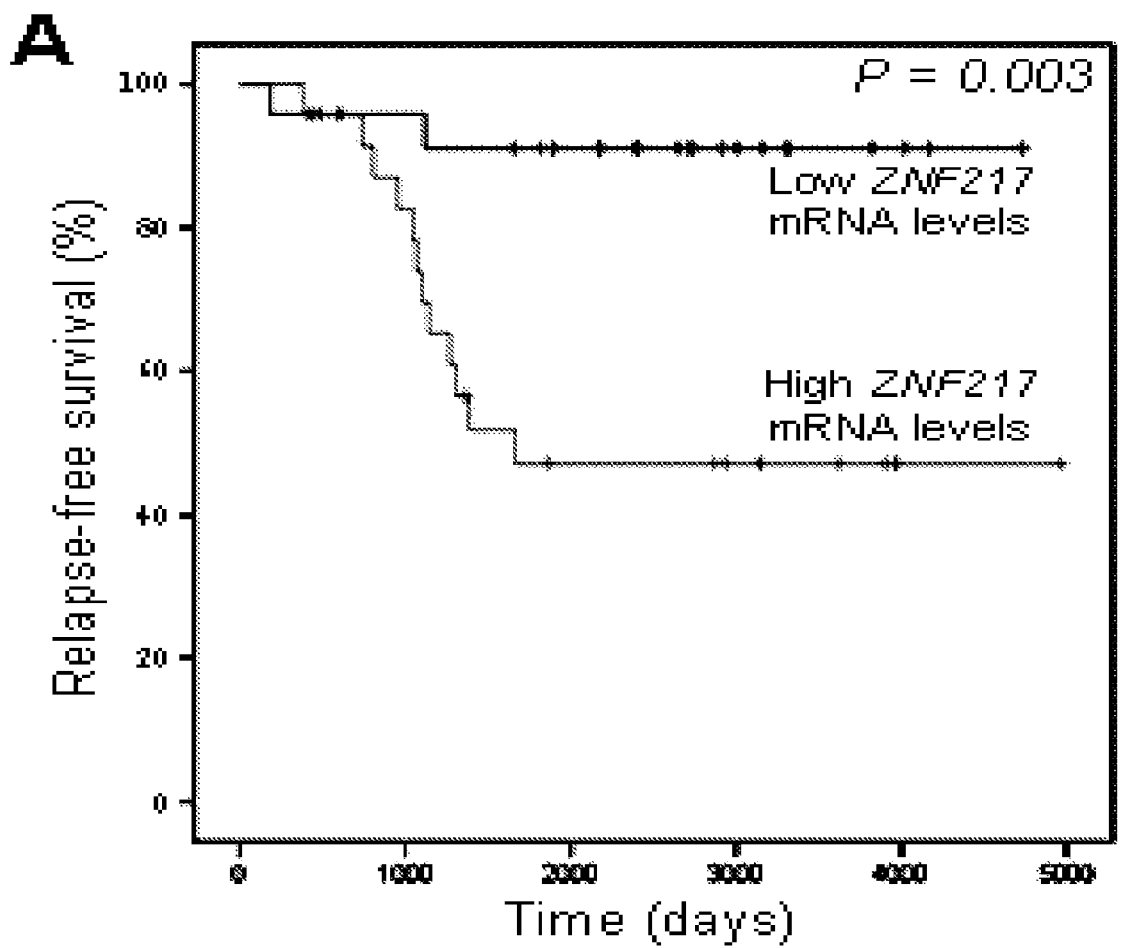
FIG. 8A is a Kaplan-Meier curve (log-rank test analysis) for RFS in breast tumors from the CLB1 cohort.
Figure 8B:
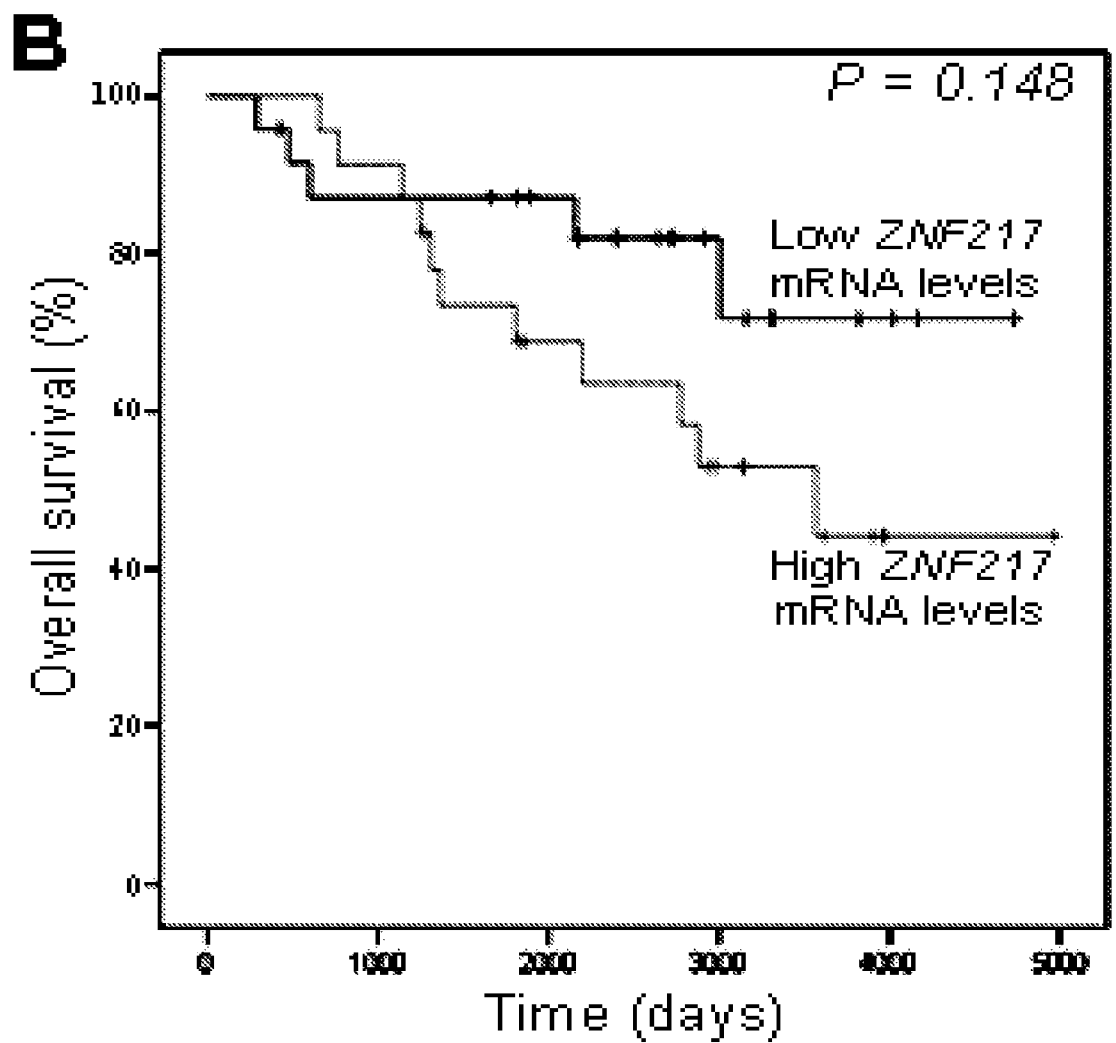
FIG. 8B is a Kaplan-Meier curve (log-rank test analysis) for OS in breast cancer tumors from the CLB1 cohort.

FIG. 8: Prognostic value of ZNF217 mRNA level. (A) Kaplan-Meier curve (log-rank test analysis) for RFS in breast tumors from the CLB1 cohort. (B) Kaplan-Meier curve (log-rank test analysis) for OS in breast cancer tumors from the CLB1 cohort.

Figure 9:
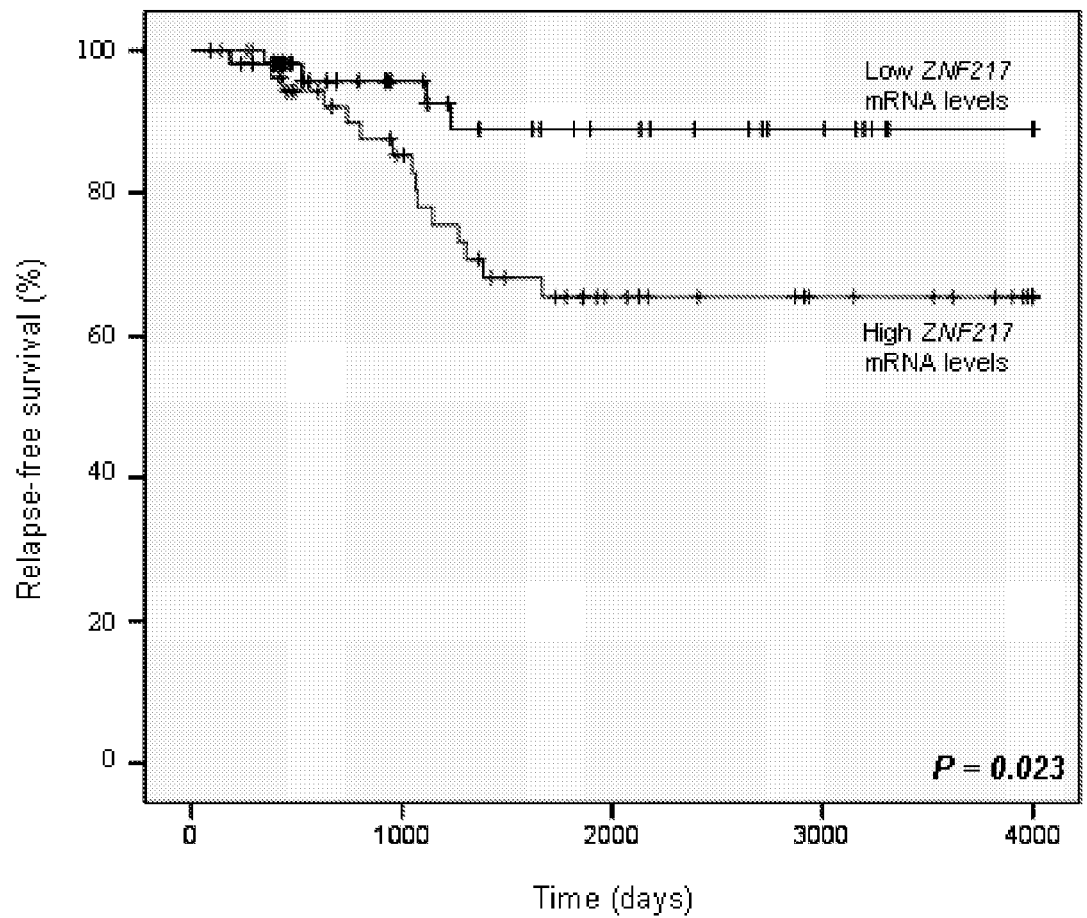
FIG. 9 is a Kaplan-Meier curve (log-rank test analysis) for RFS.

FIG. 9: Prognostic value of ZNF217 mRNA level in the breast tumors (n=113) from the CLB2 cohort. Kaplan-Meier curve (log-rank test analysis) for RFS.

Figure 10:
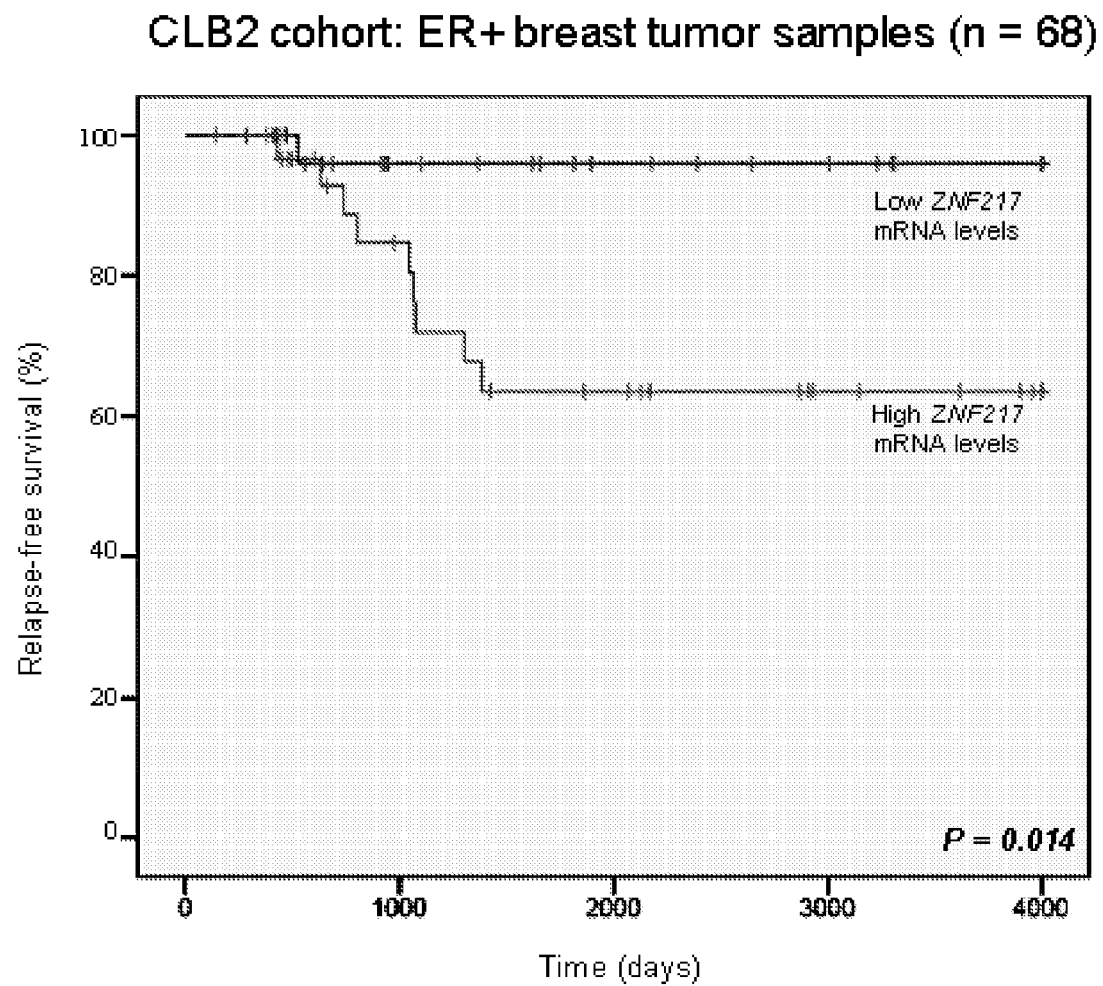
FIG. 10 is a Kaplan-Meier curve (log-rank test analysis) for RFS.

FIG. 10: Prognostic value of ZNF217 mRNA level in the ER-positive (ER+) breast tumors (n=68) from the CLB2 cohort. Kaplan-Meier curve (log-rank test analysis) for RFS.

Figure 11:
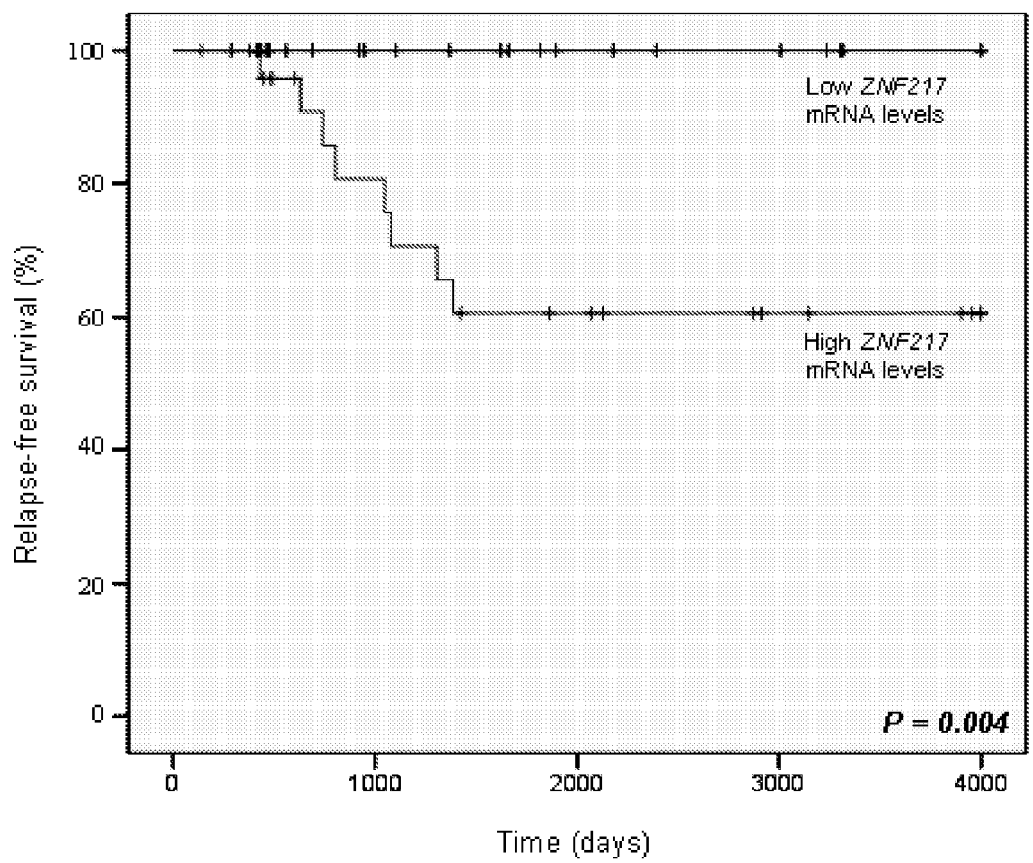
FIG. 11 is a Kaplan-Meier curve (log-rank test analysis) for RFS.

FIG. 11: Prognostic value of ZNF217 mRNA level in the ER+ and HER2-negative (HER2−) breast tumors (n=57) from the CLB2 cohort. Kaplan-Meier curve (log-rank test analysis) for RFS.

FIG. 12: ZNF217 and ER expression levels are correlated in breast cancer cells. Total protein extracts from cell lines were analyzed by Western blotting with an anti-ZNF217 and anti-ERα antibody. Expression of α-tubulin was used as an invariant control. (A) Over-expression of ZNF217 in MDA-MB-231 breast cancer stable transfectants constitutively expressing ER (S30 cells). (B) Western-blot analysis of ZNF217 and ERα expression in transfected MCF7 cells with either scrambled RNA (MCF7 scrambled) or with an siRNA-ZNF217 (MCF7 siRNA-ZNF217).

Figure 13A:
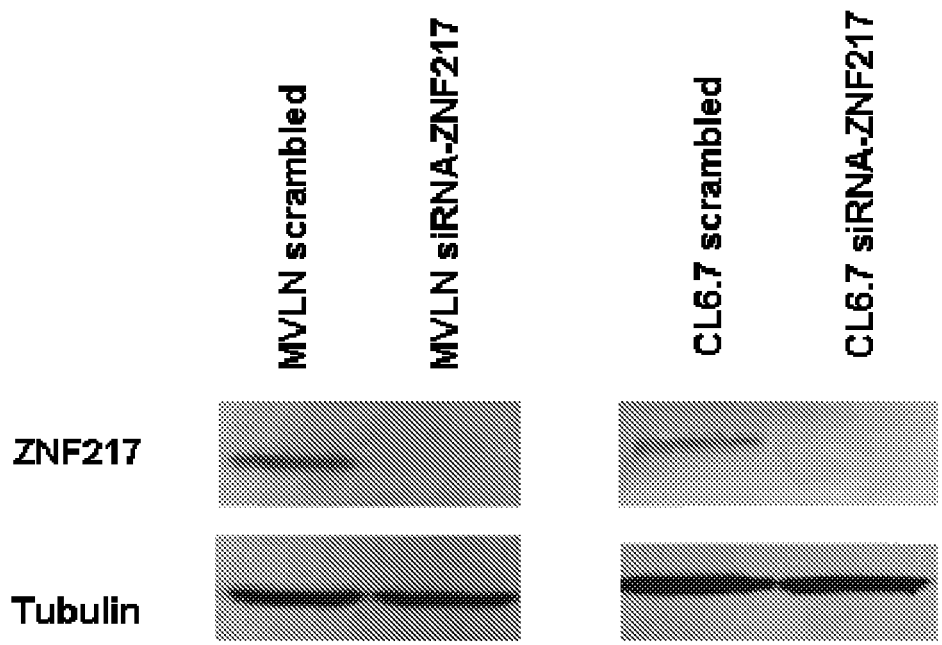
FIG. 13A is a Western-blot analysis of ZNF217 in transfected MVLN and CL6.7 cells with either scrambled RNA or with an siRNA-ZNF217.
Figure 13B:
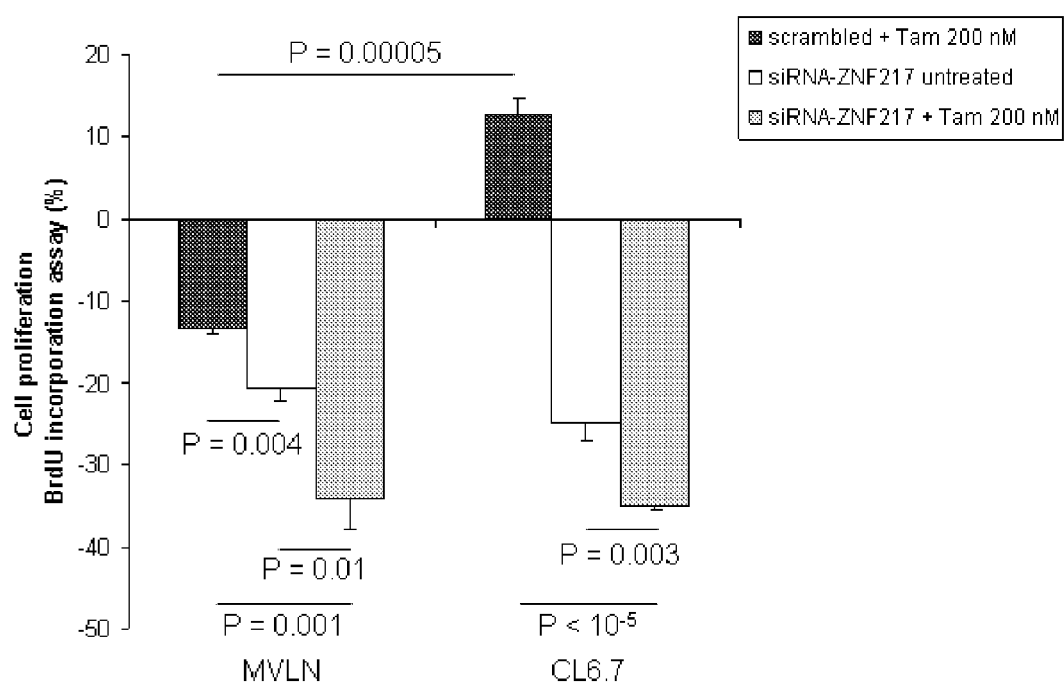
FIG. 13B is a graph of cell proliferation (BrdU test) of transfected MVLN and CL6.7 cells with either scrambled RNA or siRNA-ZNF217, in the presence or the absence of 200 nM OH-Tam.

FIG. 13: Endocrine resistance is reversed in the presence of an siRNA-ZNF217 in OH-Tam-resistant CL6.7 cells. Total protein extracts from cell lines were analyzed by Western blotting with an anti-ZNF217. Expression of α-tubulin was used as an invariant control. (A) Western-blot analysis of ZNF217 in transfected MVLN and CL6.7 cells with either scrambled RNA or with an siRNA-ZNF217. (B) Cell proliferation (BrdU test) of transfected MVLN and CL6.7 cells with either scrambled RNA or siRNA-ZNF217, in the presence or the absence of 200 nM OH-Tam. This assay was performed in steroid-free medium. P-value (Student's t-test) was considered as significant when P<0.05.

EXAMPLES

Materials and Methods

Cell Culture

MCF7 and MDA-MB-231 breast cancer cells were purchased from ATCC and grown according to recommendations in DMEM medium supplemented with 10% fetal bovine serum (Invitrogen, Cergy Pontoise, Paris). S30 cells and their MDA-MB-231 control cells have been previously described (Levenson et al., 2003). The cellular model of endocrine resistance (MVLN and CL6.7 cells) have been previously established and described (Demirpence et al., 1993).

MDA-MB-231-ZNF217 Stable Transfectants

The full length ZNF217 cDNA was used to construct the ZNF217 expression plasmid using the pcDNA6/V5-His plasmid (Invitrogen, Cergy Pontoise, Paris). Briefly, the full length ZNF217 cDNA was obtained by adding the missing cDNA sequence (coding for the last 6 C-terminal amino acids of the ZNF217 protein) to the pEGFP-N1-ZNF217 plasmid generously provided by Dr Collins, then subcloned into the pcDNA6/V5-His plasmid (pcDNA6/V5-His-ZNF217). MDA-MB-231 breast cancer cells (possessing a low endogenous level of ZNF217) were grown according to ATCC recommendations and then stably transfected with 6 µg of either empty pcDNA6/V5-His plasmid or pcDNA6/V5-His-ZNF217. Transfected cell populations were selected in the presence of 20 µg/ml blasticidin (Invitrogen). We then isolated two MDA-MB-231-ZNF217 cellular clones (called ZNF217-1 and ZNF217-2). Total RNA was extracted using a Qiagen (Germantown, Md., USA) RNA extraction kit according to the manufacturer's recommendations. RNA quality was assessed using the Bio Analyzer 2100™ (Agilent Technologies, Palo Alto, Calif., USA).

MCF10A-ZNF217 Stable Transfectants

MCF10A cells, which are immortalized but non-trans formed human mammary epithelial cells derived from breast tissue (Soule et al., 1990), were grown according to ATCC recommendations. Cells were stably transfected with 6 µg of either empty pcDNA6/V5-His plasmid or pcDNA6/V5-His-ZNF217. Transfected cell populations were selected in the presence of 20 µg/ml blasticidin (Invitrogen).

Real-Time Quantitative PCR (RTQ-PCR) Analysis

One microgram of total RNA from each sample was reverse-transcribed, and RTQ-PCR measurements were performed as previously described (Girault et al., 2003; Vendrell et al., 2005), using a LightCycler 480® (Roche, Meylan, France) or an ABI Prism 7700 Sequence Detection System (Perkin-Elmer Applied Biosystems, Foster City, Calif., USA) with the corresponding SYBR Green Kit, according to the manufacturer's recommendations. The forward primer (SEQ ID NO: 1) 5'-AGTCCAAATCCCTGCCATCT-3' and the reverse primer (SEQ ID NO: 2) 5'-GGGGAAACACTG-GTTTTAGG-3' were designed to specifically target the ZNF217 transcript ($NM\_006526.2$). The primers targeting the ESR1 (Estrogen receptor alpha) transcript were: forward primer (SEQ ID NO: 3) 5'-TGTTCCAAACCCATCGT-CAGT-3'; reverse primer (SEQ ID NO: 4) 5'-CTCTATAAC-CAATGACCTCTCTGTGAA-3'). The primers targeting the ERBB2 transcript were: forward primer: (SEQ ID NO: 5) 5'-ACTGGCCCTCATCCACCATA-3'; reverse primer (SEQ ID NO: 6) 5'-GGTTGGCAGTGTGGAGCAG-3'.

Western Blot

Cell extract preparation and western blot analysis were performed as previously described (Vendrell et al., 2004). ZNF217 antibody was made by Covalab (Lyon, France); E-cadherin, α-catenin, β-catenin and fibronectin antibodies were purchased from BD Biosciences (Franklin Lakes, N.J., USA). Occludin antibody was from Zymed Laboratories (San Francisco, Calif., USA), vimentin antibody from Dako (Glostrup, Denmark), cyclin E2 and ERα antibodies from Santa Cruz Biotechnology Inc. (Santa Cruz, Calif., USA), cyclin D1 antibody from Cell Signaling (Beverly, Mass., USA), and cyclin A2 and α-tubulin antibodies from Sigma Chemical Co. (St. Louis, Mo., USA).

Cell Proliferation Assay (BrdU)

Proliferating cells were analyzed using the Cell Proliferation ELISA, BrdU (colorimetric) Kit (Roche, Meylan, France). Briefly, the cells were labeled for 24 h with 5-bromodeoxyuridine (BrdU) and the labeled nuclei were identified using a specific anti-BrdU antibody according to the manufacturer's recommendations.

Soft Agar Colony Formation Assay

Six-well plates were first covered with an agar layer containing 0.75% agar (Seaplaque Agarose®, Lonza, Basel, Switzerland) in DMEM supplemented with 10% FCS (Gibco). MDA-MB-231 control, ZNF217-1 and ZNF217-2 cells were then suspended in 10% FCS-DMEM containing 0.45% agar and plated into wells (10,000 cells per well). The cultures were returned to the incubator and fed every 2 days with 10% FCS-DMEM growth medium. Twenty days later, the cells were stained with 0.005% Cristal violet (Sigma-Aldrich, Saint Quentin Fallavier, France) for 1 hour. Photomicrographs of colonies were then taken at ×1.25 magnification.

Boyden Chamber Invasion Assay

The quantification of cell invasion was carried out in Transwell cell culture chambers containing fluorescence-blocking porous polycarbonate membrane inserts (Fluoroblock; BD Biosciences; pore size 8 µm). 100 µl of 2 mg/ml Matrigel with reduced growth factors (a commercially prepared reconstituted basement membrane from Engelbreth-Holm-Swarm tumours; BD Biosciences) were prepared in a Transwell chamber. Cells were cultured as monolayers before trypsinization and plated ($10^5$) in 2% FCS-containing medium on top of a thick layer (around 500 µm) of Matrigel within the upper chamber of a Transwell apparatus. Controls were left untreated. The upper and lower chambers were then filled with respectively 2% and 10% FCS-containing media, thus establishing a soluble gradient of chemoattractant promoting cell invasion through the Matrigel. Cells were stored at 37° C. in 5% $CO_2$ and allowed to migrate through the gel before fixation for 15 min in 3.7% formaldehyde. The cells that had invaded through the Matrigel were detected by fluorescence on the lower side of the filter and counted. The whole surface of the filter was counted and each assay was performed twice in triplicate for each condition.

Matrigel Invasion Analysis

A thick layer of Matrigel (600 µl) (BD Biosciences) was coated onto an 8-well LabTec chamber slide and allowed to partially polymerize. One million cells were suspended in 1 µl DMEM and seeded in the middle of the Matrigel layer. After 30 min of incubation at 37° C., we added 150 µl of DMEM; the medium was changed every 2 days. Samples were analyzed in triplicate. Images were taken every 1, 4, 7, 11, 14 and 18 days using an inverted Diavert microscope (Leica Microsystems, Rueil-Malmaison, France, ×1.5 magnification) at the Centre Commun de Quantimétrie (Lyon, Université Claude Bernard, France). The magnitude of cell invasion through the Matrigel was measured using Image J software, developed by the National Institute of Health (USA).

Wound Healing

Wound healing assay was used to detect the alteration of cell motility. Cells were plated at $2.5 \times 10^6$ cells in DMEM onto 60-mm culture plates. Confluent monolayer was wounded using a P-200 pipette tip by scratching and photographed at 0 hour and 26 hours (×2.5 magnification) at the Centre Commun de Quantimétrie (Lyon).

Gene Silencing

Stealth™ siRNA targeting ZNF217 (siRNA-ZNF217) and scrambled control RNA (scrambled) were obtained from Invitrogen. Five nanomoles of siRNA-ZNF217 or scrambled were transfected into cell lines with lipofectamine RNAimax (Invitrogen).

CLB1 Cohort: Breast Tumor Samples from the Centre Léon Bérard (n=47)

We selected 47 primary breast tumor samples obtained from women operated at the Centre Léon Bérard (Lyon, France) (Table 1). Informed consent was obtained from all patients and the study was approved by the ethics committee of the institution. The breast tumor samples were excised from women who had not received endocrine therapy, chemotherapy or radiotherapy before surgery. Fourteen patients developed metastases while on chemotherapy and/or endocrine therapy (Met+ group), whereas 33 patients did not (Met− group). Standard prognostic factors are shown in Table 1. The patients (mean age: 53 years; range: 40-82) met the following criteria: primary unilateral breast carcinoma; complete clinical, histological, and biological information available; no radiotherapy or chemotherapy before surgery; and full follow-up at the Centre Léon Bérard. The histological type and the number of positive axillary nodes were established at the time of surgery. The malignancy of infiltrating carcinomas was scored according to the Scarff-Bloom-Richardson (SBR) histological grading system (Bloom and Richardson, 1957). Using the $\chi^2$ test, there was no significant difference in age, histological grade, lymph node status, tumor size or estrogen receptor status between the two groups (Table 1). Estrogen receptor α (ER) status was determined by immunohistochemistry. Patients in the Met+ group developed metastases between 0.6 and 4.6 years after surgery. Immediately following surgery, the tumor samples were placed in liquid nitrogen until RNA extraction. Total RNA was extracted using a Macherey-Nagel (Hoerd, France) RNA extraction kit according to the manufacturer's recommendations. RNA quality was assessed using the BioAnalyzer 2100™ (Agilent Technologies, Palo Alto, Calif., USA).

Breast Tumor Samples from the Centre René Huguenin

We selected 48 ER+ primary breast tumor samples obtained from women operated at the Centre René Huguenin (St Cloud, France) (Table 2). Informed consent was obtained from all patients and the study was approved by the ethics committee of the institution. The tumors were taken from patients treated with primary surgery followed by adjuvant endocrine therapy alone. Twenty-four patients relapsed while on endocrine therapy and developed metastases (Met+ group) and 24 did not (Met− group). Standard prognostic factors are shown in Table 2. The patients (mean age: 70.7 years; range: 54-86) met the following criteria: primary unilateral postmenopausal breast carcinoma; complete clinical, histological, and biological information available; no radiotherapy or chemotherapy before surgery; and full follow-up at the Centre René Huguenin. The histological type and the number of positive axillary nodes were established at the time of surgery. The malignancy of infiltrating carcinomas was scored according to the SBR histological grading system (Bloom and Richardson, 1957). Using the $\chi^2$ test, there was no significant difference in age, histological grade, lymph node status or tumor size between the two groups (Table 2). ER status was determined at the protein level by using quantitative biochemical methods (dextran-coated charcoal method or enzymatic immunoassay) and confirmed by RTQ-PCR. All patients received postoperative adjuvant endocrine therapy (tamoxifen, 20 mg daily for 3-5 years) and no other treatment. Patients in the Met+ group developed metastases between 1.3 and 10.0 years after surgery and the beginning of tamoxifen treatment. Immediately following surgery, the tumor samples were placed in liquid nitrogen until RNA extraction. Total RNA was extracted from frozen tumor samples by using the acid-phenol guanidinium method. RNA integrity was checked by denaturing agarose gel electrophoresis.

CLB2 Cohort: Breast Tumor Samples from the Centre Léon Bérard (n=113)

We selected 113 primary breast tumor samples obtained from women operated at the Centre Léon Bérard (Lyon, France) (Table 7). Informed consent was obtained from all patients and the study was approved by the ethics committee of the institution. The breast tumor samples were excised from women who had not received endocrine therapy, chemotherapy or radiotherapy before surgery. Nineteen patients relapsed while on chemotherapy and/or endocrine therapy (relapse group), whereas 94 patients did not (No relapse group). Standard prognostic factors are shown in Table 7. The patients (mean age: 53 years; range: 40-82) met the following criteria: primary unilateral breast carcinoma; complete clinical, histological, and biological information available; no radiotherapy or chemotherapy before surgery; and full follow-up at the Centre Léon Bérard. The histological type and the number of positive axillary nodes were established at the time of surgery. The malignancy of infiltrating carcinomas was scored according to the SBR histological grading system (Bloom and Richardson, 1957). ER and progesterone receptor (PR) status were determined by immunohistochemistry. HER2 status was determined by immunohistochemistry and validated for few samples by FISH. Using the $\chi^2$ test, there was no significant difference in age, histological grade, lymph node status, tumor size, ER status, PR status or HER2 status between the two groups (Table 7). Patients in the Relapse group developed metastases between 0.5 and 4.5 years after surgery. Immediately following surgery, the tumor samples were placed in liquid nitrogen until RNA extraction. Total RNA was extracted using a Macherey-Nagel RNA extraction kit according to the manufacturer's recommendations. RNA quality was assessed using the BioAnalyzer 2100™ (Agilent Technologies).

Classification of Breast Cancer Subtypes Among the CLB2 Cohort

Using the immunohistochemical and clinicopathological parameters currently used in clinic, breast tumors were classified in molecular subgroups: the Luminal subclass (ER+ and/or PR+), the HER2+ subclass (ER−/PR−/HER2+) and the Triple negative subclass (ER−/PR−/HER2−). The Luminal subclass was reclassified in Luminal A and Luminal B subgroups according the classification given by Hugh et al., (2009) and Cheang et al. (2009) or that given by Millar et al. (2009) and Nguyen et al. (2008). In the first classification, Luminal A breast tumors were ER+ and/or PR+, HER2− and low proliferative index (given by low KI67 or given by SBR1 and SBR2) and Luminal B possess ER+ and/or PR+ and also possess HER2+ or high proliferative index (high KI67 or SBR3) status; in the second classification Luminal A tumors were breast cancers with ER+ and/or PR+ and HER2− status and Luminal B tumors those with ER+ and/or PR+ and HER2+ only.

Statistical Analyses

Statistical analyses of RTQ-PCR measurements were performed with the Mann-Whitney test and the Spearman's rank test using the Statgraphics® 3 plus software (Statgraphics Centurion, Herndon, Va., USA). Results were judged significant at a confidence level greater than 95% (P<0.05). For each gene, the breast tumor cohorts were divided into 2 groups: one with "low" mRNA level (lower than the median of mRNA levels of all breast tumor samples) and the other with "high" mRNA level (higher than the median of mRNA levels of all breast tumor samples). Events of interest were Overall Survival (OS) and Relapse-Free Survival (RFS). OS was measured from date of diagnosis to death or censored at last follow-up. RFS was measured from date of diagnosis to relapse, or censored at last follow-up. Survival distribution was estimated by the Kaplan-Meier method and the significance of differences between survival rates was ascertained by the log-rank test (univariate analysis), using the SPSS® Software (Chicago, Ill., USA). As this study is an exploratory analysis, all statistical analyses were done at a 0.05 significance level, and no correction was applied for multiple testing. Candidate prognostic factors for RFS with a 0.10 significance level in univariate analysis were entered in a multivariate Cox model, and a backward selection procedure was used to build the final model.

Results

Figure 2B:
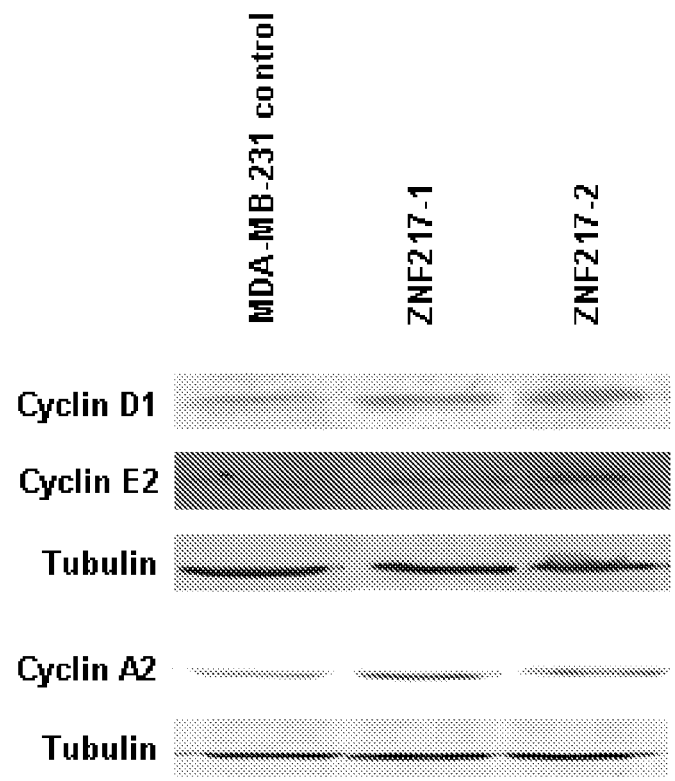
FIG. 2B is a Western blot analyzing cyclin A2, cyclin D1 and cyclin E2 protein expression levels in ZNF-217-transfected MDA-MB-231 cells.

ZNF217 Over-Expression in MDA-MB-231 Breast Cancer Cells Promotes Cell Proliferation Stable MDA-MB-231 breast carcinoma cells constitutively over-expressing the ZNF217 protein were established (see Materials and Methods). These cells were chosen because of their low level of endogenous ZNF217 expression. MDA-MB-231 cells were transfected with either the eukaryotic expression vector pcDNA6/V5-His containing the full length cDNA sequence of ZNF217 or with the empty vector used as negative control. After blasticidin selection, two cellular clones over-expressing ZNF217 mRNA and protein (ZNF217-1 and ZNF217-2) as well as a cellular clone transfected with the empty pcDNA6/V5-His (MDA-MB-231 control cells) were selected. ZNF217 mRNA levels were 2.0- to 3.5-fold greater in ZNF217-1 and ZNF217-2 cells, respectively, than in MDA-MB-231 control cells (data not shown). Accordingly, ZNF217 protein expression was increased by 5.4- and 5.1-fold in ZNF217-1 and ZNF217-2 cells, respectively, in comparison with MDA-MB-231 control cells (FIG. 1). Therefore, a good concordance between expression of ZNF217 at the mRNA level and at the protein level could be observed. In a cell proliferation assay using BrdU labeling, ZNF217 over-expression in ZNF217-1 and ZNF217-2 cells was associated with increased cell proliferation (FIG. 2A) and increased expression of cyclin A2, cyclin D1 and cyclin E2 (FIG. 2B).

ZNF217 Promotes Anchorage-Independent Growth, Migration and In Vitro Invasiveness of Breast Carcinoma Cells.

Anchorage-independent proliferation, a hallmark of malignant cells that form tumors in vivo (Irshad et al., 2004; Lee et al., 2004), is thought to be associated with highly metastatic cancer cells (Glondu et al., 2002; Muraoka-Cook et al., 2004) and can be assayed by soft agar colony formation. We thus next examined the effect of ZNF217 over-expression on soft agar colony formation in the different cell populations. We found an approximately 67-fold and 70-fold increase in the number of ZNF217-1 and ZNF217-2 colonies formed when ZNF217 was over-expressed as compared to MDA-MB-231 control cells (FIG. 3).

Destruction or penetration of the basement membrane is thought to be an essential step in tumor cell invasion. A strong capacity for migration is another hallmark of tumor malignancy (Gupta and Massague, 2006). In a number of studies, highly metastatic tumor cells exhibited upregulated migration in in vitro invasion assays carried out using Boyden chambers (Chen et al., 2006; Galaup et al., 2006) and in wound healing assays (Hu and Verkman, 2006). We therefore sought to investigate whether ZNF217 over-expression affects tumor invasion and/or migration. We studied the invasiveness of ZNF217-1, ZNF217-2 and control cells in an in vitro Boyden chamber assay (FIG. 4) where the cells were plated on top of a thick layer of Matrigel mimicking the physiological basement membrane. FIG. 4 shows that invasiveness significantly increased with ZNF217 expression, with approximately the same variations in both clones. The number of invasive cells was 6.3 and 7 higher in ZNF217-over-expressing clones compared to control cells. Supporting data were provided by Matrigel invasion assays which also clearly demonstrated the invasive properties of the ZNF217-1 and ZNF217-2 cells (FIG. 5). Overexpression of ZNF217 in the MDA-MB-231 cells led also to an increased in migration as demonstrated by wound healing assay (FIG. 6). Altogether, these results suggest the important role of ZNF217 in the invasiveness as well as the anchorage-independent growth of breast carcinoma cells.

ZNF217 Induces Epithelial-Mesenchymal Transition (EMT)

Because EMT has been demonstrated to be involved in cancer cell invasion (Yilmaz and Christofori, 2009), we next examined the effects of ZNF217 in the human mammary epithelial cells MCF10A (Soule et al., 1990; Tait et al., 1990). Over-expression of ZNF217 in stably transfected MCF10A cells was sufficient to trigger some morphological features of EMT, including a fibroblastic morphology, associated with a significant decrease of epithelial markers (E-cadherin, α-catenin, β-catenin, occludin) and an increase of mesenchymal protein levels (vimentin and fibronectin) (FIG. 7). We therefore suggest that the ability to promote EMT is another important feature underlying the enhanced invasive capacity of ZNF217.

ZNF217 is a Prognostic Marker of Metastatic Breast Cancer

With the aim to investigate the clinical relevance of ZNF217, we explored by RTQ-PCR ZNF217 mRNA levels in 47 breast tumor samples collected at the Centre Léon Bérard (France) (CLB1 cohort) (Table 1). Using the Mann-Whitney test, we compared the expression of ZNF217 with clinical and pathological parameters (Table 3); no significant association was observed in any case. As the cohort was composed of women who either had developed metastases (at 0.6 and 4.6 years from surgery) while on chemotherapy and/or endocrine therapy (Met+ group, n=14) or who had not (Met– group, n=33), we assessed ZNF217 expression levels in these two groups of patients. As shown in Table 4, high ZNF217 mRNA levels were significantly associated with the development of metastases (significant ZNF217 mRNA over-expression in the Met+ group, P=0.002, Mann-Whitney test).

We then used univariate analysis (log-rank test) to further study the prognostic value of ZNF217. Univariate analysis showed that high levels of expression of ZNF217 mRNA were significantly associated with shorter RFS (P=0.003, Table 5 and FIG. 8A). No significant association between ZNF217 mRNA level and OS could be observed, but there was a trend toward significance (P=0.15, Table 6 and FIG. 8B).

We then assessed the relevance of our findings in an independent cohort of breast cancer patients from a different geographical origin. This cohort collected by the Centre René Huguenin (France) was composed of ER+ breast cancer patients who had developed or not metastases on endocrine therapy (24 Met+ and 24 Met– samples). Again, ZNF217 expression was found significantly elevated in the Met+ group (Median=2.4; range: 0.24-14.62) compared to the Met– group (Median=1.0; range: 0.21-2.15; P=0.0003, Mann-Whitney test), and high expression levels of ZNF217 were significantly associated with shorter RFS (P=0.039, Log-rank test). We thus confirmed, in two different cohorts of breast cancer patients, first, the presence of high expression levels of ZNF217 in the primary breast tumors of patients prone to develop metastases and, second, the significant association of ZNF217 with RFS. Altogether, these data suggest that ZNF217 could represent a new marker of poor prognosis.

ERBB2 (HER2) is a well-known marker of poor prognosis in breast cancer. ERBB2 expression levels were not significantly associated with RFS or with OS (Tables 5 and 6). However, a trend toward significance could be observed for RFS (P=0.09, log-rank test; Table 5). There was also no evidence of an association between ESR1 (ER alpha) expression levels and RFS or OS (Tables 5 and 6). A Cox multivariate regression analysis of RFS was performed using candidate prognostic factors for RFS with a 0.10 significance level in univariate analysis (ZNF217 and ERBB2). The most interesting finding was that only the prognostic value of ZNF217 remained significant in the multivariate analysis (P=0.002; HR=9.56; 95% CI: 1.57 to 31.59, Table 5). Taken together, these results demonstrate first that ZNF217 is a new prognostic marker associated with RFS in breast cancer patients prone to develop metastases, and second that the prognostic value of ZNF217 was still more informative than that of ERBB2.

Finally, we investigated the relevance of our findings by a retrospective statistical analysis of gene expression array data from a previous study of 60 breast tumor samples from patients who had developed or not metastases on tamoxifen (28 Met+ and 32 Met–) (Ma et al., 2004). Based on the data of this gene expression profiling study, we found significantly greater expression levels of ZNF217 in Met+ than in Met– samples (P=$7.5 \times 10^{-4}$, Mann-Whitney test), and a significant association of high expression levels of ZNF217 with RFS (P=0.01; Log-rank test), thus validating our findings.

ZNF217 Possesses a High Prognostic Value in Breast Tumors Classified as "Tumors with Good Prognosis"

A new cohort of 113 breast tumor samples collected by the Centre Léon Bérard (named CLB2 cohort) (Table 7) was used to investigate whether the prognostic value of ZNF217 was still present and/or improved in specific subclasses of breast tumors.

Using the Mann-Whitney test, we compared the expression of ZNF217 with clinical and pathological parameters: no significant association was observed in any case (Table 8). However, we validated that high expression levels of ZNF217 were significantly associated with shorter RFS (P=0.023, log-rank test; Table 9 and FIG. 9). When assessing in this cohort the prognostic value of several clinical and pathological parameters, we only found lymph node status (3 invaded nodes) associated with shorter RFS (P=0.044, log-rank test, Table 9). Cox multivariate regression analysis of RFS was performed using ZNF217 and the node invasion status. Strikingly, only the prognostic value of ZNF217 remained significant in the multivariate analysis (P=0.019; HR=5.54; Table 9) demonstrating that the prognostic value of ZNF217 was still more informative than that of lymph node invasion status.

Breast cancer markers detected by immunohistochemistry such as ER and HER2 (ERBB2) have been classically used for cancer prognosis, and breast tumors ER– and/or HER2+ are tumors with poor prognosis. However, only 30-40% of breast cancers are ER– and 15-20% of breast cancers are HER2+. Thus there is an urgent need for new prognostic biomarkers in breast cancers currently considered of "better prognostic cancers", i.e. with an ER+ and/or HER2– status.

In the ER+ (n=68) and in the ER+/HER2– (n=57) subclasses of the CLB2 cohort, the prognostic value of ZNF217 associated with RFS was still present, and surprisingly, compared to the prognostic value obtained in the whole cohort, was improved (P=0.014 and P=0.004, respectively, log-rank test, Table 10, FIGS. 10 and 11). By retrospective analysis of an independent cohort (Ma et al., 2004), we validated that the prognostic value of ZNF217 was more significant in the ER+/HER2– subclass (P=0.001, log-rank test, Table 10) compared to the global cohort (P=0.014, log-rank test, Table 10). When stratifying the 113 breast tumors of the CLB2 cohort using ER status, HER2 status, SBR status and/or lymph nodes status, we found that high expression levels of ZNF217 were significantly associated with shorter RFS in the breast tumors subclasses displaying markers of "good prognosis", i.e. ER+ (P=0.014), HER2– (P=0.007), SBR1+SBR2 (P=0.004) or SBR2 subclasses (P=0.01) (log-rank test, Table 11). A trend toward significance could also be observed in the tumors collected from patients possessing few invaded lymph nodes (≤3) (P=0.052, log-rank test, Table 11). Conversely, no significant association between ZNF217 and RFS could be found in the breast tumor subclasses displaying conventional markers of "bad prognosis" such as ER–, HER2+, SBR3 or lymph node status (3) (log-rank test, Table 11). Finally in subclasses combining several "good prognostic" parameters such as ER+ and/or PR+, ER+ and/or PR+ and SBR1+2, ER+/SBR1+2, or ER+/HER2–/SBR1+2, high expression levels of ZNF217 were still significantly associated with shorter RFS (P=0.013, P=0.002, P=0.015 and P=0.031, respectively, log-rank test, Table 11). Interestingly, significance was nearly reached (P=0.067, log-rank test, Table 11) in the ER+/HER2–/SBR1+2/Lymph nodes (≤3) subclass (n=27). Finally, high expression levels of ZNF217 were significantly associated with OS only in the whole cohort (P=0.049, log-rank test, Table 11). Interestingly, a trend toward significance was also present in the ER+/HER2− subclass, P=0.055) (Table 11).

Recently, immunohistological (ER, PR, HER2, KI67) and/or clinical (SBR) parameters have been proposed to classify breast cancers into subtypes that are biologically distinct and behave differently (Blows et al., 2010; Cheang et al., 2009; Hugh et al., 2009; Millar et al., 2009; Nguyen et al., 2008). The prognosis and chemotherapy sensitivity of the different molecular subgroups are different. Luminal-like cancers are ER+ and/or PR (Progesterone Receptor)-positive and therefore sensitive to endocrine therapy, and may have a more favourable prognosis than the HER2+ and Triple negative subtypes, even in the absence of any therapy. Luminal B subtype is equivalent to those that express either HER2 or that possess a high proliferative phenotype given by KI67 or SBR (that takes into account the number of mitoses observed) (Cheang et al., 2009; Hugh et al., 2009; Millar et al., 2009; Nguyen et al., 2008; Voduc et al., 2010). Luminal B breast cancers have been shown to have less favourable long-term survival than luminal A breast cancers (Blows et al., 2010; Cheang et al., 2009; Hugh et al., 2009; Nguyen et al., 2008; Voduc et al., 2010). Utmost importance is then attached to markers aimed at re-stratifying the luminal subclasses, in particular the luminal A subclass. In the CLB2 cohort, we found that high expression levels of ZNF217 were significantly associated with shorter RFS in luminal breast cancers (P=0.013, log-rank test, Table 12) but not in the HER2+ or Triple negative subtypes. Interestingly, no prognostic value was detected for ZNF217 in the Luminal B subclasses while high ZNF217 expression levels were associated with shorter RFS in the Luminal A subclasses (P=0.012 and P=0.014, log-rank test, Table 12). Altogether, these data demonstrated that ZNF217 expression level is a new marker of poor prognosis in breast cancer patients, in particular in breast tumors possessing at least one of conventional markers of good prognosis (ER+ and/or PR+, HER2−, SBR1+2, lymph node status (≤3), luminal A). ZNF217 thus possesses an added value to the current conventional markers and would allow the re-stratification of patients with breast cancers considered as cancers with good prognosis. Thus, the ZNF217 status should help clinicians for therapeutic decision.

A Cross-Talk Exists Between ZNF217 and ER Signaling Pathways

Figure 12A:
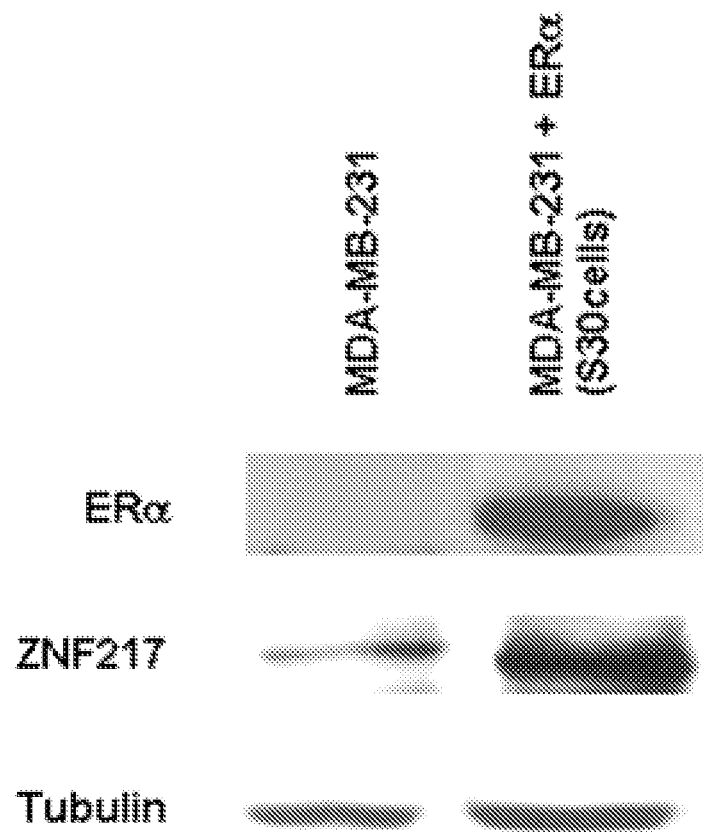
FIG. 12A is a Western blot analysis of total protein extracts from cell lines with an anti-ZNF217 and anti-ERα antibody.
Figure 12B:
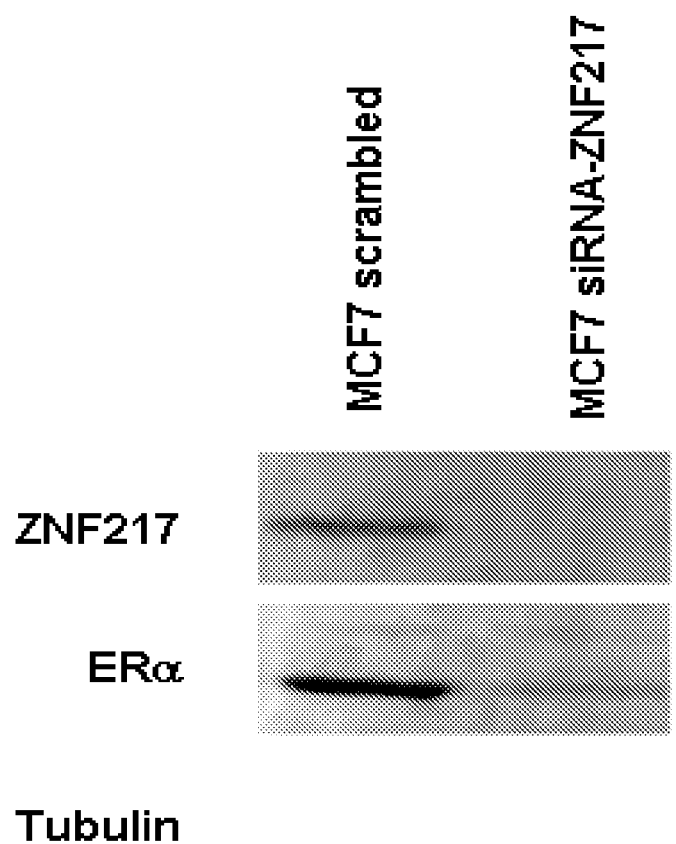
FIG. 12B is a Western-blot analysis of ZNF217 and ERa expression in transfected MCF7 cells with either scrambled RNA (MCF7 scrambled) or with an siRNA-ZNF217 (MCF7 siRNA-ZNF217).

Given to the fact that the poor prognostic value of ZNF217 is predominant in ER+ breast cancers, we explored the relationship between ZNF217 and ER expression. By RTQ-PCR we found a significant correlation between ZNF217 mRNA levels and ESR1 mRNA levels in two independent cohorts of breast tumor samples: Spearman rank correlation coefficient=+0.47; P=0.0001 (in a 33 ER+ and 34 ER− breast tumor cohort) and Spearman rank correlation coefficient=+0.69; P=0.0001 (in a 39 ER+ breast tumor cohort). The ER− MDA-MB-231 cell line has been previously stably transfected with wild-type ESR1 to generate a new cell line (S30 cells) constitutively expressing ERalpha (Levenson et al., 2003). We demonstrated by western blot that the constitutive expression of ER in the S30 cells was associated with increased expression levels of ZNF217 protein in comparison to the control MDA-MB-231 cells (FIG. 12A). Conversely, in the ER+ MCF7 breast cancer cell line, possessing high endogenous levels of ZNF217, knocking-out ZNF217 expression by a siRNA strategy was associated with decreased ER expression (FIG. 12B).

The development of pharmacological resistance and relapse under endocrine therapy represents a real issue in the clinical management of ER+ breast cancers. Interestingly, we found that ZNF217 is a marker of poor prognosis and of relapse in two cohorts of patients treated only by adjuvant endocrine therapy: the cohort collected by the Centre René Huguenin (P=0.039, Log-rank test), and by retrospective analysis, the cohort described by Ma et al. (P=0.014, Log-rank test) (Ma et al., 2004). By a retrospective statistical analysis of gene expression array data from another previous study of 155 breast tumor samples from patients who had developed or not metastases on tamoxifen (44 Met+ and 155 Met−) (Chanrion et al., 2008), we validated once more that high ZNF217 mRNA levels are markers of poor prognosis and of relapse (P=0.01, Log-rank test).

MVLN is an ER+, hormone-responsive and OH-Tamoxifen(OH-Tam)-sensitive breast carcinoma cell line derived from MCF7 cells (Demirpence et al., 1993). Six-month exposure of MVLN cells to OH-Tam allowed the emergence of an OH-Tam-resistant but still estrogen-dependent CL6.7 cellular clone. The OH-Tam resistance phenotype developed by the CL6.7 cells was characterized under OH-Tam exposure by the loss of the cytostatic activity of the molecule that is detectable in MVLN cells and the occurrence of a strong stimulation of CL6.7 cell proliferation (estrogen-like effect) (Ghayad et al., 2010) (FIG. 13). In a cell proliferation assay using BrdU labeling, combining the ZNF217 knocking-out (siRNA strategy) with OH-Tam exposure led to increased sensitivity to endocrine therapy in the sensitive MVLN cell line (P=0.001, Student test) and to the reversion of hormono-resistance in the CL6.7 cell line (the OH-Tam estrogen-like activity was now reversed to a 35% inhibition of cell proliferation, P<$10^{-5}$) (FIG. 13).

Altogether, these data suggest that a cross-talk exists between ZNF217 and ER expression levels and that high ZNF217 expression levels are associated with reduced response to endocrine therapy. Altogether, these data strongly suggest that ZNF217 might represent a predictive marker for endocrine therapy.

CONCLUSION

In conclusion, we have demonstrated in in vitro experiments that ZNF217 over-expression in breast cancer cells triggers a proliferative, anchorage-independent growth and is associated with an invasive and EMT phenotype. We have shown that ZNF217 expression represents a new marker of poor prognosis in breast cancer patients prone to relapse and to develop metastases. More precisely, ZNF217 expression level is a potent poor prognosis marker of breast cancers classified by the current available clinical markers/parameters as cancers with good/better prognosis (e.g. the ER+ subclass, the HER2− subclass, the luminal subclass (ER+ and/or PR+), the ER+/HER2− subclass, the SBR1 and/or SBR2 subclass, no/few lymph node invasion subclass (≤3), the ER+ and/or PR+ and SBR1 and/or SBR2 subclass, the ER+/HER2−/SBR1 and/or SBR2 subclass, the ER+/HER2−/SBR1 and/or SBR2/no/few lymph node invasion (≤3) subclass, the luminal A subclass). Assessing ZNF217 expression levels alone or in association with other prognostic markers thus would permit the re-stratification of these cancers classified as having good/better prognosis into two subclasses: "good prognosis" breast cancers (with low ZNF217 expression levels) or "bad prognosis" breast cancers (with high ZNF217 expression levels), thus helping clinicians for therapeutic decision. The prognostic value of ZNF217 in luminal breast cancers could be (at least in part) explained by the cross-talk existing between ZNF217 and ER. Moreover, as deregulated ZNF217 expression levels are associated with reduced response to endocrine therapy (found in 3 cohorts) or to endocrine/chemotherapy (found in 2 cohorts), ZNF217 might also represent a predictive marker for anti-cancer therapies, and in particular, for endocrine therapy.

TABLE 1

Patients from the CLB1 cohort: Characteristics of the 47 patients with primary breast cancer

| | Number of patients | | |
|---|---|---|---|
| | Met− group (n = 33) | Met+ group (n = 14) | P[a] |
| Age (years) | | | |
| ≤70 | 29 | 14 | NS (0.43) |
| >70 | 4 | 0 | |
| Histological grade[b] | | | |
| I + II | 15 | 10 | NS (0.22) |
| III | 17 | 4 | |
| Lymph node status | | | |
| <3 | 16 | 6 | NS (0.85) |
| ≥3 | 17 | 7 | |
| Macroscopic tumor size | | | |
| <30 mm | 7 | 2 | NS (0.88) |
| ≥30 mm | 26 | 12 | |
| Estrogen Receptor status[c] | | | |
| Positive | 25 | 7 | NS (0.16) |
| Negative | 8 | 7 | |

[a]P-value ($\chi^2$ test) was considered significant when P < 0.05.
[b]Scarff-Bloom-Richardson classification.
[c]Determined by immunohistochemistry.

TABLE 2

Patients from the Centre René Huguenin (Saint-Cloud, France): Characteristics of the 48 patients with ER+ primary breast cancer

| | Number of patients | | |
|---|---|---|---|
| | Met− group (n = 24) | Met+ group (n = 24) | P[a] |
| Age (years) | | | |
| ≤70 | 13 | 14 | NS (1) |
| >70 | 11 | 10 | |
| Histological grade[b] | | | |
| I + II | 22 | 16 | NS (0.08) |
| III | 2 | 8 | |
| Lymph node status | | | |
| <3 | 19 | 13 | NS (0.13) |
| ≥3 | 5 | 11 | |
| Macroscopic tumor size | | | |
| <30 mm | 18 | 14 | NS (0.36) |
| ≥30 mm | 6 | 10 | |

[a]P-value ($\chi^2$ test) was considered significant when P < 0.05.
[b]Scarff-Bloom-Richardson classification.

TABLE 3

Relationships between ZNF217 mRNA levels and clinical and pathological parameters in breast tumor samples from the CLB1 cohort

| | Number of samples | mRNA levels (arbitrary units) | | |
|---|---|---|---|---|
| | | Median | Range | P[a] |
| Age (years) | | | | |
| ≤70 | 43 | 3.88 | 0.21-36.15 | NS (0.13) |
| >70 | 4 | 2.30 | 1.26-3.33 | |
| Histological grade[b] | | | | |
| I + II | 25 | 4.35 | 0.21-23.01 | NS (0.26) |
| III | 22 | 3.23 | 0.72-36.15 | |
| Lymph node status | | | | |
| <3 | 26 | 3.21 | 0.21-17.08 | NS (0.07) |
| ≥3 | 21 | 4.59 | 0.92-36.15 | |
| Macroscopic tumor size | | | | |
| <30 mm | 9 | 3.21 | 0.92-13.91 | NS (0.35) |
| ≥30 mm | 38 | 3.82 | 0.21-36.15 | |
| Estrogen Receptor status[c] | | | | |
| Positive | 32 | 3.71 | 0.21-36.15 | NS (0.62) |
| Negative | 15 | 3.75 | 0.72-23.33 | |

[a]P-value (Mann-Whitney test) was considered significant when P < 0.05. NS, not significant.
[b]Scarff-Bloom-Richardson classification.
[c]Determined by immunohistochemistry.

TABLE 4

RTQ-PCR analysis of mRNA levels. Statistical comparison between Met− and Met+ tumor samples from the CLB1 cohort

| Genes | Tumor samples | Number of samples | mRNA levels (arbitrary units) | | |
|---|---|---|---|---|---|
| | | | Median | Range | P[a] |
| ZNF217 | Met− | 33 | 3.21 | 0.21-23.01 | 0.002 |
| | Met+ | 14 | 8.09 | 1.35-36.15 | |
| ERBB2 | Met− | 33 | 1.52 | 0.07-84.82 | NS (0.06) |
| | Met+ | 14 | 5.30 | 0.40-143.26 | |
| ESR1 | Met− | 33 | 0.597 | 0.01-149.76 | NS (0.31) |
| | Met+ | 14 | 0.19 | 0.01-2.46 | |

[a]P-value (Mann-Whitney test) was considered significant when P < 0.05. NS, not significant.

TABLE 5

Univariate and multivariate analyses of the ZNF217, ERBB2 and ESR1 gene expressions in relation to relapse-free survival in the 47 breast tumor samples from the CLB1 cohort

| | Univariate (n = 47) | | | Multivariate (n = 47) | | |
|---|---|---|---|---|---|---|
| Genes | HR[a] | 95% CI[b] | P[c] | HR | 95% CI | P |
| ZNF217 | 8.821 | 1.57 to 31.59 | 0.003 | 9.56 | 1.57 to 31.59 | 0.002 |
| ERBB2 | 2.821 | 0.82 to 8.32 | NS (0.09) | | | NS |
| ESR1 | 0.732 | 0.21 to 0.19 | NS (0.39) | ND[d] | ND | ND |

[a]HR, Hazard ratio.
[b]95% CI, 95% confidence interval.
[c]P-value was considered significant when P < 0.05. NS, not significant.
[d]ND, not done. Multivariate analysis was done using the variables with a significance level inferior to 0.10 in univariate analysis.

TABLE 6

Univariate analysis of the ZNF217, ERBB2 and ESR1 gene expressions in relation to overall survival in the 47 breast tumor samples of the CLB1 cohort

| Genes | Univariate (n = 47) | | |
|---|---|---|---|
| | HR[a] | 95% CI[b] | P[c] |
| ZNF217 | 2.09 | 0.74 to 6.19 | NS (0.15) |
| ERBB2 | 0.02 | 0.35 to 2.48 | NS (0.88) |
| ESR1 | 0.11 | 0.31 to 2.27 | NS (0.74) |

[a]HR, Hazard ratio.
[b]95% CI, 95% confidence interval.
[c]P-value was considered significant when P < 0.05.
NS, not significant.

TABLE 7

Patients from the CLB2 cohort: Characteristics of the 113 patients with primary breast cancer

| | Number of patients | | |
|---|---|---|---|
| | No relapse group (n = 94) | Relapse group (n = 19) | P[a] |
| Age (years) | | | |
| ≤50 | 43 | 12 | NS (0.26) |
| >50 | 51 | 7 | |
| Histological grade[b,c] | | | |
| I + II | 36 | 11 | NS (0.20) |
| III | 57 | 8 | |
| Lymph node status | | | |
| ≤3 | 60 | 7 | NS (0.054) |
| >3 | 34 | 12 | |
| Macroscopic tumor size[c] | | | |
| ≤20 mm | 6 | 1 | NS (0.75) |
| >20 mm | 87 | 18 | |
| Estrogen Receptor status[d] | | | |
| Positive | 58 | 10 | NS (0.63) |
| Negative | 36 | 9 | |
| Progesterone Receptor status[d] | | | |
| Positive | 59 | 11 | NS (0.89) |
| Negative | 35 | 8 | |
| HER2 status[c,e] | | | |
| Positive | 23 | 7 | NS (0.33) |
| Negative | 71 | 11 | |

[a]P-value ($\chi^2$ test) was considered significant when P < 0.05.
[b]Scarff-Bloom-Richardson classification.
[c]Information available for 112 patients.
[d]Measured by immunohistochemistry.
[e]Measured by immunohistochemistry (validated by FISH for few samples).

TABLE 8

Relationships between ZNF217 mRNA levels and clinical and pathological parameters in breast tumors samples from the CLB2 cohort

| | Number of samples | mRNA levels (arbitrary units) | | |
|---|---|---|---|---|
| | | Median | Range | P[a] |
| Age (years) | | | | |
| ≤50 | 55 | 0.46 | 0.01-56.50 | NS (0.80) |
| >50 | 58 | 0.41 | 0.01-49.40 | |
| Histological grade[b,c] | | | | |
| I + II | 47 | 0.54 | 0.01-49.40 | NS (0.59) |
| III | 65 | 0.38 | 0.01-56.50 | |
| Lymph node status | | | | |
| ≤3 | 67 | 0.41 | 0.01-49.40 | NS (0.86) |
| >3 | 46 | 0.45 | 0.01-56.50 | |
| Macroscopic tumor size[c] | | | | |
| ≤20 mm | 7 | 0.66 | 0.16-49.40 | NS (0.14) |
| >20 mm | 105 | 0.40 | 0.01-56.50 | |
| Estrogen Receptor status[d] | | | | |
| Positive | 68 | 0.42 | 0.01-56.50 | NS (0.53) |
| Negative | 45 | 0.45 | 0.01-12.43 | |
| Progesterone Receptor status[d] | | | | |
| Positive | 70 | 0.41 | 0.01-56.50 | NS (0.72) |
| Negative | 43 | 0.45 | 0.01-12.43 | |
| HER2 status[c,e] | | | | |
| Positive | 30 | 0.49 | 0.04-56.50 | NS (0.65) |
| Negative | 82 | 0.41 | 0.01-49.40 | |

[a]P-value (Mann-Whitney test) was considered significant when P < 0.05. NS, not significant.
[b]Scarff-Bloom-Richardson classification.
[c]Information available for 112 patients.
[d]Measured by immunohistochemistry.
[e]Measured by immunohistochemistry (validated by FISH for few samples).

TABLE 9

Univariate and multivariate analyses of the ZNF217 gene expression and clinical parameters in relation to relapse-free survival in the 113 breast cancer samples from the CLB2 cohort

| | Number of samples | Univariate | | | Multivariate | | |
|---|---|---|---|---|---|---|---|
| | | HR[a] | 95% CI[b] | P[c] | HR | 95% CI | P |
| ZNF217 mRNA levels | 113 | 5.14 | 1.11 to 10.04 | 0.023 | 5.54 | 1.11 to 10.04 | 0.019 |
| Age (≤50 year-old; >50 year-old) | 113 | 0.92 | 0.25 to 1.61 | NS (0.337) | ND[d] | ND | ND |

TABLE 9-continued

Univariate and multivariate analyses of the ZNF217 gene expression and clinical parameters in relation to relapse-free survival in the 113 breast cancer samples from the CLB2 cohort

|  | Number of samples | Univariate HR[a] | 95% CI[b] | P[c] | Multivariate HR | 95% CI | P |
|---|---|---|---|---|---|---|---|
| Macroscopic tumor size (≤20 mm; >20 mm) | 112 | 0.02 | 0.15 to 8.74 | NS (0.881) | ND | ND | ND |
| Lymph node status (≤3; >3) | 113 | 4.04 | 0.99 to 6.40 | 0.044 |  |  | NS (0.057) |
| Histological grade (SBR1 + 2; SBR3) | 112 | 1.49 | 0.23 to 1.42 | NS (0.222) | ND | ND | ND |
| Estrogen Receptor status (negative; positive) | 113 | 0.35 | 0.31 to 1.88 | NS (0.557) | ND | ND | ND |
| HER2 status (negative; positive) | 113 | 0.59 | 0.56 to 3.73 | NS (0.443) | ND | ND | ND |
| Luminal (A; B)[e] | 74 | 0.04 | 0.37 to 3.33 | NS (0.842) | ND | ND | ND |
| Luminal (A; B)[f] | 74 | 0.07 | 0.32 to 4.31 | NS (0.798) | ND | ND | ND |

[a]HR, Hazard ratio.
[b]95% CI, 95% confidence interval.
[c]P-value was considered significant when P < 0.05. NS, not significant.
[d]ND, not done. Multivariate analysis was done using the variables with a significance level inferior to 0.10 in univariate analysis.
[e]classification according to Hugh et al. (2009) and Cheang et al. (2009).
[f]classification according to Millar et al. (2009) and Nguyen et al. (2008).

TABLE 10

Univariate analysis of the ZNF217 gene expression in different subclasses of breast cancers in relation to relapse-free survival (RFS) in the CLB2 cohort and the cohort described by Ma et al. (2004)

|  | Number of samples | RFS HR[a] | 95% CI[b] | P[c] |
|---|---|---|---|---|
| CLB2 Cohort |  |  |  |  |
| All breast tumor samples | 113 | 5.14 | 1.11 to 10.04 | 0.023 |
| ER+ subclass | 68 | 6.05 | 1.09 to 67.93 | 0.014 |
| ER+/HER2− subclass | 57 | 8.27 | N/A[d] | 0.004 |
| Ma's Cohort |  |  |  |  |
| All breast tumor samples | 60 | 5.99 | 1.17 to 5.76 | 0.014 |
| ER+ subclass | 56 | 5.03 | 1.09 to 5.87 | 0.025 |
| ER+/HER2− subclass | 50 | 10.91 | 1.66 to 10.67 | 0.001 |

[a]HR, Hazard ratio.
[b]95% CI, 95% confidence interval.
[c]P-value was considered significant when P < 0.05.

TABLE 11

Univariate analysis of the ZNF217 gene expression in relation to relapse-free survival (RFS) and overall survival (OS) in different subclasses of the 113 breast cancer samples from the CLB2 cohort

|  | Number of samples | RFS HR[a] | 95% CI[b] | P[c] | OS HR | 95% CI | P |
|---|---|---|---|---|---|---|---|
| All breast tumor samples | 113 | 5.14 | 1.11 to 10.04 | 0.023 | 3.89 | 0.97 to 6.45 | 0.049 |
| ER+ subclass | 68 | 6.05 | 1.09 to 67.93 | 0.014 | 2.73 | 0.77 to 11.06 | NS (0.098) |
| ER− subclass | 45 | 0.36 | 0.55 to 1.53 | NS (0.548) |  |  |  |
| HER2+ subclass | 30 | 0.7 | 0.38 to 10.29 | NS (0.403) |  |  | ND[d] |
| HER2− subclass | 82 | 7.22 | 1.26 to 76.98 | 0.007 |  |  | ND |
| ER+/HER2− subclass | 57 | 8.27 | N/A[e] | 0.004 | 3.68 | 0.86 to 19.56 | NS (0.055) |
| SBR1 + 2 subclass | 47 | 8.34 | 1.42 to 86.75 | 0.004 |  |  | ND |
| SBR2 subclass | 37 | 6.57 | 1.16 to 74.37 | 0.010 |  |  | ND |
| SBR3 subclass | 65 | 0.26 | 0.35 to 6.08 | NS (0.609) |  |  | ND |
| Lymph node status (≤3) subclass | 67 | 3.79 | 0.75 to 52.09 | NS (0.052) |  |  | ND |
| Lymph node status (>3) subclass | 46 | 0.62 | 0.48 to 5.36 | NS (0.431) |  |  | ND |
| ER+ and/or PR+ subclass | 74 | 6.11 | 1.20 to 24.50 | 0.013 |  |  | ND |
| ER+ and/or PR+/SBR1 + 2 subclass | 41 | 9.51 | N/A | 0.002 |  |  | ND |
| ER+/SBR1 + 2 subclass | 38 | 5.88 | N/A | 0.015 |  |  | ND |
| ER+/HER2−/SBR1 + 2 subclass | 34 | 4.65 | N/A | 0.031 |  |  | ND |
| ER+/HER2−/SBR1 + 2/Lymph node status (≤3) subclass | 27 | 3.35 | N/A | NS (0.067) |  |  | ND |

[a]HR, Hazard ratio.
[b]95% CI, 95% confidence interval.
[c]P-value was considered significant when P < 0.05. NS, not significant.
[d]ND, not done.
[e]N/A, Not applicable as all the cases are censored in the low ZNF217 mRNA level group.

TABLE 12

Univariate analysis of the ZNF217 gene expression in relation to relapse-free survival (RFS) in different subclasses of the 113 breast cancer samples from the CLB2 cohort

| | Number of samples | HR[a] | RFS 95% CI[b] | P[c] |
|---|---|---|---|---|
| Luminal subclass (ER+ and/or PR+) | 74 | 6.11 | 1.20 to 24.50 | 0.013 |
| HER2+ (ER−/PR−/HER2+) | 16 | 0.20 | 0.17 to 16.03 | NS (0.658) |
| Triple Negative (ER−/PR−/HER2−) | 21 | 1.00 | N/A[f] | NS (0.320) |
| Luminal A subclass (ER+ and/or PR+/HER2−/SBR1 or SBR2)[d] | 35 | 6.34 | N/A | 0.012 |
| Luminal B subclass (ER+ and/or PR+/HER2+ and/or SBR3)[d] | 39 | 1.03 | 0.44 to 11.79 | NS (0.311) |
| Luminal A subclass (ER+ and/or PR+/HER2−)[e] | 60 | 6.04 | 1.09 to 67.87 | 0.014 |
| Luminal B subclass (ER+ and/or PR+/HER2+)[e] | 14 | 0.39 | 0.19 to 23.27 | NS (0.534) |

[a]HR, Hazard ratio.
[b]95% CI, 95% confidence interval.
[c]P-value was considered significant when P < 0.05. NS, not significant.
[d]classified according to Hugh et al. (2009) and Cheang et al. (2009).
[e]classified according to Millar et al. (2009) and Nguyen et al. (2008).
[f]N/A, Not applicable as all the cases are censored in the low ZNF217 mRNA level group.

REFERENCES

Non-Patent Literature Cited in the Description

Bloom, H. J. G., and Richardson, W. W. (1957). Histological grading and prognosis in breast cancer. Br J Cancer 11, 359-377.

Blows, F. M., Driver, K. E., Schmidt, M. K., Broeks, A., van Leeuwen, F. E., Wesseling, J., Cheang, M. C, Gelmon, K., Nielsen, T. O., Blomqvist, C, et al. (2010). Subtyping of breast cancer by immunohistochemistry to investigate a relationship between subtype and short and long term survival: a collaborative analysis of data for 10,159 cases from 12 studies. PLoS Med 7, e1000279.

Chanrion, M., Negre, V., Fontaine, H., Salvetat, N., Bibeau, F., Mac Grogan, G., Mauriac, L., Katsaros, D., Molina, F., Theillet, C, and Darbon, J. M. (2008). A gene expression signature that can predict the recurrence of tamoxifen-treated primary breast cancer. Clin Cancer Res 14, 1744-1752.

Cheang, M. C, Chia, S. K., Voduc, D., Gao, D., Leung, S., Snider, J., Watson, M., Davies, S., Bernard, P. S., Parker, J. S., et al. (2009). Ki67 index, HER2 status, and prognosis of patients with luminal B breast cancer. J Natl Cancer Inst 101, 736-750.

Chen, X., Lin, J., Kanekura, T., Su, J., Lin, W., Xie, H., Wu, Y., Li, J., Chen, M., and Chang, J. (2006). A small interfering CD147-targeting RNA inhibited the proliferation, invasiveness, and metastatic activity of malignant melanoma. Cancer Res 66, 11323-11330.

Collins, C, Rommens, J. M., Kowbel, D., Godfrey, T., Tanner, M., Hwang, S. I., Polikoff, D., Nonet, G., Cochran, J., Myambo, K., et al. (1998). Positional cloning of ZNF217 and NABC1: genes amplified at 20q13.2 and overexpressed in breast carcinoma. Proc Natl Acad Sci USA 95, 8703-8708.

Collins, C., Volik, S., Kowbel, D., Ginzinger, D., Ylstra, B., Cloutier, T., Hawkins, T., Predki, P., Martin, C, Wernick, M., et al. (2001). Comprehensive genome sequence analysis of a breast cancer amplicon. Genome Res 11, 1034-1042.

Demirpence, E., Duchesne, M. J., Badia, E., Gagne, D., and Pons, M. (1993). MVLN cells: a bio luminescent MCE-7-derived cell line to study the modulation of estrogenic activity. J Steroid Biochem Mol Biol 46, 355-364.

Galaup, A., Cazes, A., Le Jan, S., Philippe, J., Connault, E., Le Coz, E., Mekid, H., Mir, L. M., Opolon, P., Corvol, P., et al. (2006). Angiopoietin-like 4 prevents metastasis through inhibition of vascular permeability and tumor cell motility and invasiveness. Proc Natl Acad Sci USA 103, 18721-18726.

Ghayad, S. E., Vendrell, J. A., Larbi, S. B., Dumontet, C, Bieche, I., and Cohen, P. A. (2010). Endocrine resistance associated with activated ErbB system in breast cancer cells is reversed by inhibiting MAPK or PI3K/Akt signaling pathways. Int J Cancer 126, 545-562.

Ginestier, C, Cervera, N., Finetti, P., Esteyries, S., Esterni, B., Adelaide, J., Xerri, L., Viens, P., Jacquemier, J., Charafe-Jauffret, E., et al. (2006). Prognosis and gene expression profiling of 20q13-amplified breast cancers. Clin Cancer Res 12, 4533-4544.

Girault, I., Tozlu, S., Lidereau, R., and Bieche, I. (2003). Expression analysis of DNA methyltransferases 1, 3A, and 3B in sporadic breast carcinomas. Clin Cancer Res 9, 4415-4422.

Glondu, M., Liaudet-Coopman, E., Derocq, D., Platet, N., Rochefort, H., and Garcia, M. (2002). Down-regulation of cathepsin-D expression by antisense gene transfer inhibits tumor growth and experimental lung metastasis of human breast cancer cells. Oncogene 21, 5127-5134.

Gupta, G. P., and Massague, J. (2006). Cancer metastasis: building a framework. Cell 127, 679-695.

Hu, J., and Verkman, A. S. (2006). Increased migration and metastatic potential of tumor cells expressing aquaporin water channels. Faseb J 20, 1892-1894.

Huang, G., Krig, S., Kowbel, D., Xu, H., Hyun, B., Volik, S., Feuerstein, B., Mills, G. B., Stokoe, D., Yaswen, P., and Collins, C. (2005). ZNF217 suppresses cell death associated with chemotherapy and telomere dysfunction. Hum Mol Genet 14, 3219-3225.

Hugh, J., Hanson, J., Cheang, M. C, Nielsen, T. O., Perou, C. M., Dumontet, C, Reed, J., Krajewska, M., Treilleux, I., Rupin, M., et al. (2009). Breast cancer subtypes and response to docetaxel in node-positive breast cancer: use of an immunohistochemical definition in the BCIRG 001 trial. J Clin Oncol 27, 1168-1176.

Irshad, S., Pedley, R. B., Anderson, J., Latchman, D. S., and Budhram-Mahadeo, V. (2004). The Brn-3b transcription factor regulates the growth, behavior, and invasiveness of human neuroblastoma cells in vitro and in vivo. J Biol Chem 279, 21617-21627.

Lee, J. Y., Kim, H., Ryu, C. H., Kim, J. Y., Choi, B. H., Lim, Y., Huh, P. W., Kim, Y. H., Lee, K. H., Jun, T. Y., et al. (2004). Merlin, a tumor suppressor, interacts with transactivation-responsive RNA-binding protein and inhibits its oncogenic activity. J Biol Chem 279, 30265-30273.

Letessier, A., Sircoulomb, F., Ginestier, C, Cervera, N., Monville, F., Gelsi-Boyer, V., Esterni, B., Geneix, J., Finetti, P., Zemmour, C, et al. (2006). Frequency, prognostic impact, and subtype association of 8p12, 8q24, 11q13, 12p13, 17q12, and 20q13 amplifications in breast cancers. BMC Cancer 6, 245.

Levenson, A. S., Gehm, B. D., Pearce, S. T., Horiguchi, J., Simons, L. A., Ward, J. E., 3rd, Jameson, J. L., and Jordan, V. C. (2003). Resveratrol acts as an estrogen receptor (ER) agonist in breast cancer cells stably transfected with ER alpha. Int J Cancer 104, 587-596.

Li, J., Zhong, M., Song, L. L., and Su, G. D. (2006). [Oncogene ZNF217 amplification on chromosome 20 q in ovarian serous cystadenocarcinoma and its clinical implications]. Nan Fang Yi Ke Da Xue Xue Bao 26, 824-825.

Ma, X. J., Wang, Z., Ryan, P. D., Isakoff, S. J., Barmettler, A., Fuller, A., Muir, B., Mohapatra, G., Salunga, R., Tuggle, J. T., et al. (2004). A two-gene expression ratio predicts clinical outcome in breast cancer patients treated with tamoxifen. Cancer Cell 5, 607-616.

Mackay, A., Tamber, N., Fenwick, K., Iravani, M., Grigoriadis, A., Dexter, T., Lord, C. J., Reis-Filho, J. S., and Ashworth, A. (2009). A high-resolution integrated analysis of genetic and expression profiles of breast cancer cell lines. Breast Cancer Res Treat 118, 481-498.

Millar, E. K., Graham, P. H., O'Toole, S. A., McNeil, C. M., Browne, L., Morey, A. L., Eggleton, S., Beretov, J., Theocharous, C, Capp, A., et al. (2009). Prediction of local recurrence, distant metastases, and death after breast-conserving therapy in early-stage invasive breast cancer using a five-biomarker panel. J Clin Oncol 27, 4701-4708.

Muraoka-Cook, R. S., Kurokawa, H., Koh, Y., Forbes, J. T., Roebuck, L. R., Barcellos-Hoff, M. H., Moody, S. E., Chodosh, L. A., and Arteaga, C. L. (2004). Conditional overexpression of active transforming growth factor beta1 in vivo accelerates metastases of transgenic mammary tumors. Cancer Res 64, 9002-9011.

Nguyen, P. L., Taghian, A. G., Katz, M. S., Niemierko, A., Abi Raad, R. F., Boon, W. L., Bellon, J. R., Wong, J. S., Smith, B. L., and Harris, J. R. (2008). Breast cancer subtype approximated by estrogen receptor, progesterone receptor, and HER-2 is associated with local and distant recurrence after breast-conserving therapy. J Clin Oncol 26, 2373-2378.

Plevova, P., Cerna, D., Balcar, A., Foretova, L., Zapletalova, J., Silhanova, E., Curik, R., and Dvorackova, J. (2010). CCND1 and ZNF217 gene amplification is equally frequent in BRCA1 and BRCA2 associated and non-BRCA breast cancer. Neoplasma 57, 325-332.

Quinlan, K. G., Verger, A., Yaswen, P., and Crossley, M. (2007). Amplification of zinc finger gene 217 (ZNF217) and cancer: when good fingers go bad. Biochim Biophys Acta 1775, 333-340.

Soule, H. D., Maloney, T. M., Wolman, S. R., Peterson, W. D., Jr., Brenz, R., McGrath, C. M., Russo, J., Pauley, R. J., Jones, R. F., and Brooks, S. C. (1990). Isolation and characterization of a spontaneously immortalized human breast epithelial cell line, MCF-10. Cancer Res 50, 6075-6086.

Sun, G., Zhou, J., Yin, A., Ding, Y., and Zhong, M. (2008). Silencing of ZNF217 gene influences the biological behavior of a human ovarian cancer cell line. Int J Oncol 32, 1065-1071.

Tait, L., Soule, H. D., and Russo, J. (1990). Ultrastructural and immunocytochemical characterization of an immortalized human breast epithelial cell line, MCF-10. Cancer Res 50, 6087-6094.

Tanner, M. M., Grenman, S., Koul, A., Johannsson, O., Meltzer, P., Pejovic, T., Borg, A., and Isola, J. J. (2000). Frequent amplification of chromosomal region 20q12-q13 in ovarian cancer. Clin Cancer Res 6, 1833-1839.

Tanner, M. M., Tirkkonen, M., Kallioniemi, A., Holli, K., Collins, C, Kowbel, D., Gray, J. W., Kallioniemi, O. P., and Isola, J. (1995). Amplification of chromosomal region 20q13 in invasive breast cancer: prognostic implications. Clin Cancer Res 1, 1455-1461.

Vendrell, J. A., Bieche, I., Desmetz, C, Badia, E., Tozlu, S., Nguyen, C, Nicolas, J. C, Lidereau, R., and Cohen, P. A. (2005). Molecular changes associated with the agonist activity of hydroxy-tamoxifen and the hyper-response to estradiol in hydroxy-tamoxifen-resistant breast cancer cell lines. Endocr Relat Cancer 12, 75-92.

Vendrell, J. A., Magnino, F., Danis, E., Duchesne, M. J., Pinloche, S., Pons, M., Birnbaum, D., Nguyen, C., Theillet, C, and Cohen, P. A. (2004). Estrogen regulation in human breast cancer cells of new downstream gene targets involved in estrogen metabolism, cell proliferation and cell transformation. J Mol Endocrinol 32, 397-414.

Voduc, K. D., Cheang, M. C, Tyldesley, S., Gelmon, K., Nielsen, T. O., and Kennecke, H. (2010). Breast cancer subtypes and the risk of local and regional relapse. J Clin Oncol 28, 1684-1691.

Yilmaz, M., and Christofori, G. (2009). EMT, the cytoskeleton, and cancer cell invasion. Cancer Metastasis Rev 28, 15-33.

Patent References

WO98/02539
WO2006/065940
WO03/079748

The invention claimed is:

1. A method for determining the prognosis of a breast cancer in a patient comprising the following steps:
assaying a tumor sample from the patient for at least one prognostic marker of breast cancer and assessing the level of expression of the ZNF217 gene in said sample; and if the sample displays at least one prognostic marker classifying the breast cancer as having a favorable prognosis, re-classifying the breast cancer as having a poor prognosis if the ZNF217 gene is over-expressed in said sample, wherein the level of expression of the ZNF217 gene in the sample is assessed by quantification of the ZNF217 gene transcript(s) by reverse transcription and amplification, wherein the amplification is performed using a combination of primers comprising a first primer as forward primer and a second primer as reverse primer, the first primer comprising the sequence as depicted in SEQ ID NO 1 or the reverse primer comprising the sequence as depicted in SEQ ID NO 2, followed by quantitative detection of the amplicon obtained.

2. The method for determining the prognosis of a breast cancer in a patient according to claim 1 wherein said prognostic marker classifying the breast cancer as having a favorable prognosis is determined by a histological grading system, a immunohistochemical grading system and/or detection of ERBB2 amplification.

3. The method for determining the prognosis of a breast cancer in a patient according to claim 1 wherein said prognostic marker classifying the breast cancer as having a favorable prognosis is selected in the group consisting of ER+, PR+, HER2−, low proliferative index, no/few lymph node invasion (≤3), luminal and luminal A.

4. The method for determining the prognosis of a breast cancer in a patient according to claim 1 wherein said at least one prognostic marker classifying the breast cancer as having a favorable prognosis allows the subtype classification of the breast cancer among the subtypes consisting of ER+ and/or PR+, HER2−, ER+/HER2−, SBR1 and/or SBR2, no/few lymph node invasion (≤3), ER+ and/or PR+/SBR1 and/or SBR2, ER+/HER2−/SBR1 and/or SBR2, ER+/HER2−/SBR1 and/or SBR2/no/few lymph node invasion (≤3), luminal A.

5. The method for determining the prognosis of a breast cancer in a patient according to claim 1 wherein the cancer is re-classified as prone to recur and/or prone to develop an invasive or metastatic phenotype if the ZNF217 gene is over-expressed in said sample.

6. The method for determining the prognosis of a breast cancer in a patient according to claim 1 wherein the cancer is re-classified as having a poor prognosis for relapse-free survival if the ZNF217 gene is over-expressed in said sample.

7. The method for determining the prognosis of a breast cancer in a patient according to claim 1 wherein the cancer is re-classified as having a poor prognosis for overall survival if the ZNF217 gene is over-expressed in said sample.

8. The method for determining the prognosis of a breast cancer in a patient according to claim 1 wherein the cancer is re-classified as having a poor prognosis under endocrine therapy if the ZNF217 gene is over-expressed in said sample.

9. The method for determining the prognosis of a breast cancer in a patient according to claim 1 wherein the cancer is re-classified as having a poor prognosis under chemotherapy and/or endocrine therapy if the ZNF217 gene is over-expressed in said sample.

10. A method for determining the prognosis of a breast cancer in a patient comprising the following steps:
assaying a tumor sample from said patient for at least one prognostic marker of breast cancer and assessing the level of expression of the ZNF217 gene in the sample; and if the sample displays at least one prognostic marker classifying the breast cancer as having a favorable prognosis, re-classifying the breast cancer as having a poor prognosis if the ZNF217 gene is over-expressed in said sample, wherein the level of expression of the ZNF217 gene in the sample is assessed by quantification of the ZNF217 gene transcript(s) by reverse transcription and amplification, wherein the amplification is performed using a combination of primers comprising a first primer as a forward primer and a second primer as a reverse primer, the first primer comprising the sequence as depicted in SEQ ID NO 1 and the second primer comprising the sequence as depicted in SEQ ID NO 2, followed by quantitative detection of the amplicon obtained.

11. The method for determining the prognosis of a breast cancer in a patient according to claim 10 wherein said prognostic marker classifying the breast cancer as having a favorable prognosis is determined by a histological grading system, a immunohistochemical grading system and/or detection of ERBB2 amplification.

12. The method for determining the prognosis of a breast cancer in a patient according to claim 10 wherein said prognostic marker classifying the breast cancer as having a favorable prognosis is selected in the group consisting of ER+, PR+, HER2−, low proliferative index, no/few lymph node invasion (≤3), luminal, luminal A.

13. The method for determining the prognosis of a breast cancer in a patient according to claim 10 wherein said at least one prognostic marker classifying the breast cancer as having a favorable prognosis allows the subtype classification of the breast cancer among the subtypes consisting of ER+ and/or PR+, HER2−, ER+/HER2−, SBR1 and/or SBR2, no/few lymph node invasion (≤3), ER+ and/or PR+/SBR1 and/or SBR2, ER+/HER2−/SBR1 and/or SBR2, ER+/HER2−/SBR1 and/or SBR2/no/few lymph node invasion (≤3), luminal A.

14. The method for determining the prognosis of a breast cancer in a patient according to claim 1 wherein the level of expression of the ZNF217 gene is compared to a control sample.

15. The method for determining the prognosis of a breast cancer in a patient according to claim 1 wherein the control sample is the median level of expression of ZNF217 in samples taken from patients having breast cancers.

16. The method for determining the prognosis of a breast cancer in a patient according to claim 1 wherein the sample is a breast tumor sample.

17. The method for determining the prognosis of a breast cancer in a patient according to claim 10 wherein the level of expression of the ZNF217 gene is compared to a control sample.

18. The method for determining the prognosis of a breast cancer in a patient according to claim 10 wherein the control sample is the median level of expression of ZNF217 in samples taken from patients having breast cancers.

19. The method for determining the prognosis of a breast cancer in a patient according to claim 10 wherein the sample is a breast tumor sample.

20. The method of claim 1, wherein the amplification is performed using a combination of primers comprising a first primer as forward primer and a second primer as reverse primer, the first primer comprising the sequence as depicted in SEQ ID NO 1 and the second primer comprising the sequence as depicted in SEQ ID NO 2.

21. The method of claim 10, wherein the amplification is performed using a combination of primers comprising a first primer as forward primer and a second primer as reverse primer, the first primer comprising the sequence as depicted in SEQ ID NO 1 and the second primer comprising the sequence as depicted in SEQ ID NO 2.

22. The method of claim 1, wherein the first primer consists of the sequence as depicted in SEQ ID NO 1, or the second primer consists of the sequence as depicted in SEQ ID NO 2, or the first primer consists of the sequence as depicted in SEQ ID NO 1 and the second primer consists of the sequence as depicted in SEQ ID NO 2.

23. The method of claim 10, wherein the first primer consists of the sequence as depicted in SEQ ID NO 1, or the second primer consists of the sequence as depicted in SEQ ID NO 2, or the first primer consists of the sequence as depicted in SEQ ID NO 1 and the second primer consists of the sequence as depicted in SEQ ID NO 2.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
agtccaaatc cctgccatct                                          20

<210> SEQ ID NO 2
<211> LENGTH: 20
<212> TYPE: DNA

```
-continued

<213> ORGANISM: Artificial
<220> FEATURE:
<223> OTHER INFORMATION: primer

<400> SEQUENCE: 2
ggggaaacac tggttttagg                                              20

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
tgttccaaac ccatcgtcag t                                            21

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4
ctctataacc aatgacctct ctgtgaa                                      27

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
actggccctc atccaccata                                              20

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
ggttggcagt gtggagcag                                               19
```